US012576231B2

(12) United States Patent
Williams, Jr.

(10) Patent No.: US 12,576,231 B2
(45) Date of Patent: Mar. 17, 2026

(54) INLINE MUFFLER AND POSITIVE AIRWAY PRESSURE THERAPY APPARATUS INCLUDING SAME

(71) Applicant: SOMNETICS INTERNATIONAL, INC., Fridley, MN (US)

(72) Inventor: Paul Raymond Williams, Jr., Cottage Grove, MN (US)

(73) Assignee: SOMNETICS INTERNATIONAL, INC., Fridley, MN (US)

( * ) Notice: Subject to any disclaimer, the term of this patent is extended or adjusted under 35 U.S.C. 154(b) by 930 days.

(21) Appl. No.: 17/830,955

(22) Filed: Jun. 2, 2022

(65) Prior Publication Data

US 2023/0017164 A1     Jan. 19, 2023

Related U.S. Application Data

(60) Provisional application No. 63/219,963, filed on Jul. 9, 2021.

(51) Int. Cl.
| | |
|---|---|
| *A61M 16/08* | (2006.01) |
| *A61M 16/00* | (2006.01) |
| *F01N 1/08* | (2006.01) |
| *A61M 16/06* | (2006.01) |

(52) U.S. Cl.
CPC .... *A61M 16/0875* (2013.01); *A61M 16/0066* (2013.01); *A61M 16/0816* (2013.01); *F01N 1/083* (2013.01); *A61M 16/06* (2013.01); *A61M 2205/42* (2013.01); *A61M 2207/00* (2013.01)

(58) Field of Classification Search
CPC .............. A61M 16/0066; A61M 16/08; A61M 16/0816; A61M 16/0866; A61M 16/0875; A61M 2205/42; A61M 2207/00; F01N 1/083
See application file for complete search history.

(56) References Cited

U.S. PATENT DOCUMENTS

| | | | |
|---|---|---|---|
| 8,028,695 | B2 | 10/2011 | Acker et al. |
| 8,844,529 | B2 | 9/2014 | Selvarajan et al. |
| 9,855,397 | B2 | 1/2018 | Peake et al. |
| 10,518,061 | B2 | 12/2019 | Harrington et al. |
| 10,864,343 | B2 | 12/2020 | Bath et al. |

(Continued)

FOREIGN PATENT DOCUMENTS

| | | | | |
|---|---|---|---|---|
| CA | 2 907 433 C | 4/2021 | | |
| CN | 205055109 U | * 3/2016 | ........ | A61M 16/0003 |

(Continued)

OTHER PUBLICATIONS

Machine translation of CN-205055109-U.*

(Continued)

*Primary Examiner* — Joseph D. Boecker
(74) *Attorney, Agent, or Firm* — Mueting Raasch Group

(57) ABSTRACT
An inline muffler for use with a positive airway pressure (PAP) apparatus. The muffler may provide an expansion chamber with baffles that capture acoustic energy using, for instance, a disruptive gas flow path to effectively reduce downstream noise associated with a flow of pressurized gas produced by the PAP apparatus. In some embodiments, the muffler is constructed of two mostly identical halves with baffle segments being integrally formed therewith.

21 Claims, 14 Drawing Sheets

(56)                    References Cited

U.S. PATENT DOCUMENTS

| | | | |
|---|---|---|---|
| 11,071,838 B2 | 7/2021 | Frater et al. | |
| 2004/0226562 A1* | 11/2004 | Bordewick ....... | A61M 16/0057 |
| | | | 128/204.23 |
| 2008/0127976 A1* | 6/2008 | Acker ................. | A61M 16/08 |
| | | | 128/204.18 |
| 2008/0257346 A1* | 10/2008 | Lathrop ........... | A61M 16/0066 |
| | | | 181/224 |
| 2009/0007912 A1* | 1/2009 | Lindell ................ | A61M 16/10 |
| | | | 128/204.18 |
| 2012/0145155 A1* | 6/2012 | Peake .............. | A61M 16/0875 |
| | | | 128/205.12 |
| 2012/0152255 A1* | 6/2012 | Barlow ............ | A61M 16/0622 |
| | | | 128/205.25 |
| 2012/0167879 A1* | 7/2012 | Bowman .......... | A61M 16/0655 |
| | | | 128/205.12 |
| 2015/0320954 A1* | 11/2015 | Suzuki ................. | F04D 25/062 |
| | | | 128/205.25 |
| 2021/0001069 A1 | 1/2021 | Higashiyama et al. | |
| 2024/0058558 A1 | 2/2024 | Bi et al. | |
| 2025/0041545 A1* | 2/2025 | Ward ............... | A61M 16/0875 |

FOREIGN PATENT DOCUMENTS

| | | | | |
|---|---|---|---|---|
| CN | 112587774 A | 4/2021 | | |
| WO | WO 99/22793 A1 | 5/1999 | | |
| WO | WO-2020024914 A1 * | 2/2020 | ............ | A61M 16/08 |
| WO | WO 2023/283001 A1 | 1/2023 | | |

OTHER PUBLICATIONS

International Patent Application No. PCT/US2022/031948, filed Jun. 2, 2022; International Preliminary Report on Patentability issued Jan. 18, 2024; 9 pages.

Team Lawson, "2012 Installer Catalog," Insynerator, Lawson Industries Inc., 2011, 52 pages.
"Acoustics—Determination of sound power levels and sound energy levels of noise sources using sound pressure—Engineering methods for an essentially free field over a reflecting plane," ISO 3744:2010(E), International Organization for Standardization, Fig. B.2 only, Oct. 2010, 1 page.
"Q-lite by Breas," Q-Lite Insert v2 06112020; #40-0150 Rev. B, Breas Medical, Inc., 2020, 2 pages.
"Qtube," Qtube Insert v1 08312018; #40-0046 Rev B, Breas Medical, Inc., 2018, 2 pages.
"Understanding Muffler Design and Sound Absorption Strategies," [Online]. Dragzine.com, Kimbrough, Mar. 11, 2014. [Retrieved on Jul. 13, 2023]. Retrieved from the internet: <URL:https://www.dragzine.com/tech-stories/exhaust/understanding-muffler-design-and-sound-absorption-strategies/>; 22, pages.
"Airway Larry—Airway Management Trainer Head, LF03667U," Instruction Manual, Nasco Healthcare, 1999, 8 pages.
"Transcend 3 miniCPAP," User Manual, 103940 Rev B, Somnetics International, Inc., Feb. 2019, 50 pages.
International Search Report and Written Opinion of the International Searching Authority for corresponding International Application No. PCT/US2022/031948, Aug. 25, 2022, 10 pages.
"AirFit™ F20 Full Face Mask," User Guide, Resmed Pty Ltd, 2020, 59 pages.
"Motorized Calibration Syringes With Optional Metabolic Simulator Kits," [Online]. Vacumed.com. Jan. 2, 2021, [Retrieved on Jul. 13, 2023]. Retrieved from the internet: <URL:https://www.vacumed.com/zcom/product/Product.do?compid=27&prodid=29 4>, date unknown, 5 pages.
Extended European Search Report (advance copy dated Mar. 20, 2025), for European Patent Application No. 22838212.3 filed; 11 pages.

* cited by examiner

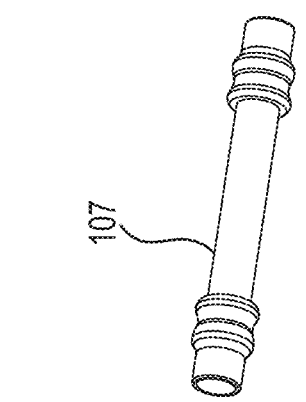
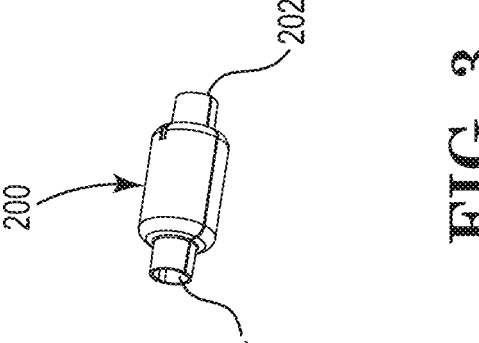
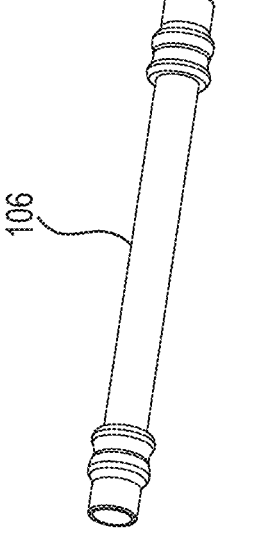
FIG. 3

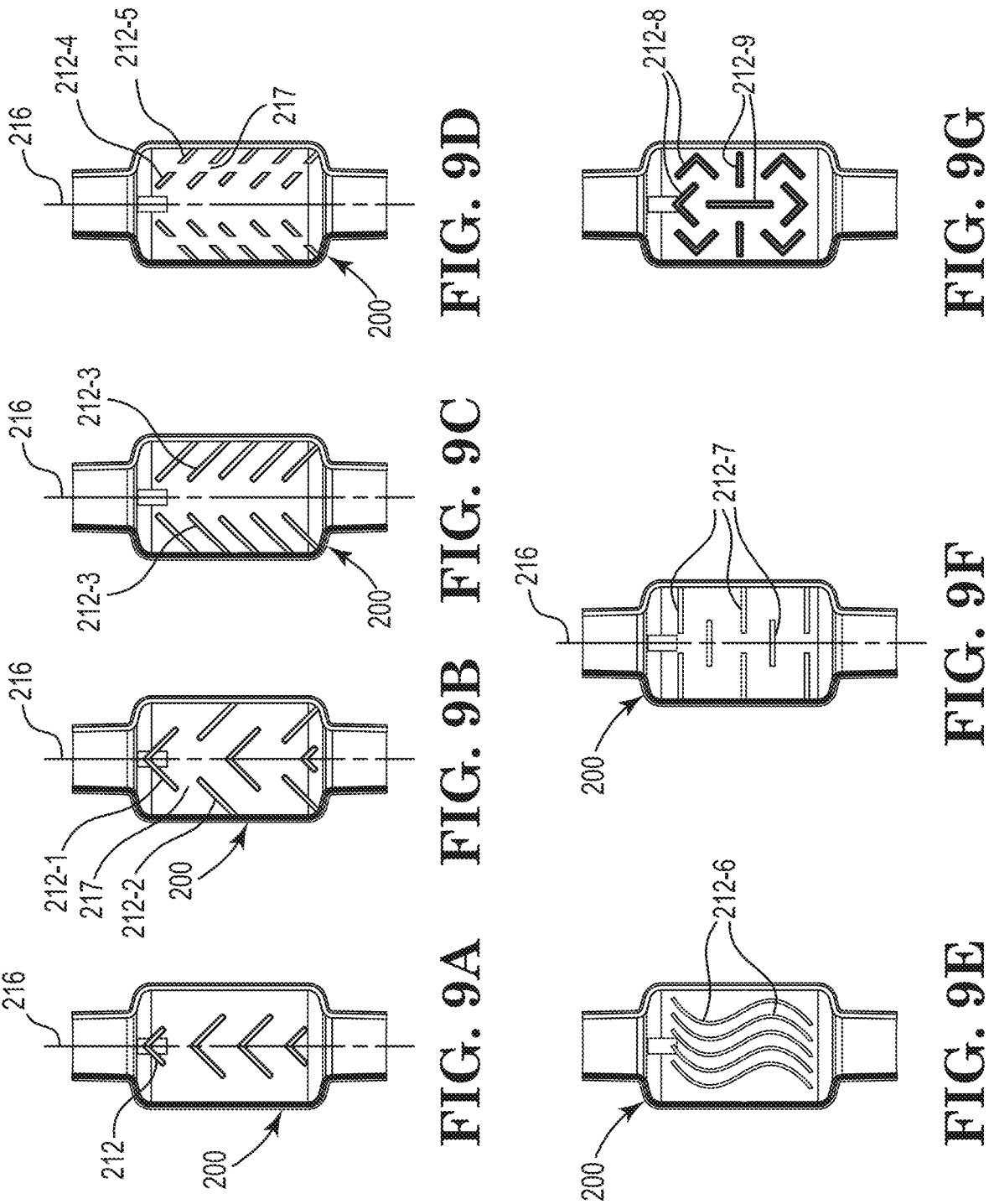

INLINE MUFFLER AND POSITIVE AIRWAY PRESSURE THERAPY APPARATUS INCLUDING SAME

The present application claims priority to and/or the benefit of U.S. Provisional Patent Application No. 63/219,963, filed 9 Jul. 2021, which is incorporated herein by reference in its entirety.

Embodiments of the present disclosure relate to positive airway pressure systems and, more particularly, to inline mufflers for use with the same.

BACKGROUND

Positive airway pressure (PAP) therapies are frequently used in the treatment of, among other ailments, obstructive sleep apnea, complex sleep apnea, asthma, bronchitis, chronic obstructive pulmonary disease (COPD), snoring, and congestive heart failure. These therapies typically provide a flow of pressurized gas (e.g., typically air, but may be most any gas or gas-vapor mixture including, for example, oxygen and medicinal vapors) to pressurize the airway of a user to a pressure in the range of 4-30 centimeters (cm) of water ($H_2O$) (e.g., often about 4-20 cm $H_2O$) or more. Depending upon the particular therapy, a variable or a constant pressure therapy may be administered to the user to reduce or eliminate airway occlusions (or to otherwise treat acute or chronic respiratory failure) that necessitated the use of the therapy.

Regardless of the particular therapy, positive airway pressure apparatus typically includes at least a blower unit and a user interface. A delivery tube or hose may also be included to connect the blower unit to the user interface, wherein the hose and interface may together define a delivery conduit. The blower unit may rest on a bedside table or floor adjacent the bed (or in the bed), or alternatively, may attach to the user. The blower may typically include a fan or impeller connected to an output shaft of a motor. A controller regulates the motor to control fan speed and thus therapy pressure. The user interface is configured to be secured relative to the user's head in such a way as to form a generally air-tight seal with the user's airway. As a result, the fan may generate a flow of pressurized gas that is delivered to the airway via the delivery conduit.

SUMMARY

Embodiments of the present disclosure may provide a positive airway pressure apparatus including: a flow generator comprising a housing containing a blower, the blower adapted to produce a flow of pressurized gas at a blower outlet; a user interface; an elongate delivery tube positioned between the flow generator and the user interface, the delivery tube adapted to communicate the flow of pressurized gas from the blower to the user interface; and an inline muffler positioned between the blower and the delivery tube, wherein the muffler comprises a tubular member adapted to attenuate noise associated with the flow of pressurized gas as the gas passes through the muffler. The muffler includes: an inlet port adapted to operatively couple to the blower outlet; an outlet port adapted to operatively couple to a proximal end of the delivery tube; and a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with the flow of pressurized gas passing through the expansion chamber.

In another embodiment, an inline muffler adapted to be positioned within a gas delivery path of a positive airway pressure apparatus between a blower and a user interface is provided, the muffler including a tubular housing defined by first and second halves secured to one another. The housing includes: a first end defining an inlet port; a second end defining an outlet port; and a body extending between the first end and the second end. The body defines an expansion chamber between the first and second ends of the housing, wherein a plurality of baffles extends between opposing inner walls of the expansion chamber. At least one of the plurality of baffles is formed by a first baffle segment integrally formed with the first half that aligns with a second baffle segment integrally formed with the second half, the two baffle segments including distal portions that terminate at or near one another within the expansion chamber.

In yet another embodiment, an inline muffler adapted to be positioned within a gas delivery path of a positive airway pressure apparatus between a blower and a user interface is provided, wherein the muffler includes a tubular member adapted to attenuate noise detected at the user interface associated with a flow of pressurized gas produced by the blower. The muffler includes: an inlet port adapted to operatively couple to an outlet of the blower; an outlet port adapted to operatively couple to a proximal end of a delivery tube that fluidly communicates with the user interface; and a body extending between the inlet port and the outlet port. The body defines an expansion chamber having an effective inner diameter larger than an effective inner diameter of both the inlet port and the outlet port, and an inner wall of the body comprises a plurality of inwardly extending baffles, the baffles adapted to capture sound energy associated with the flow of pressurized gas passing through the expansion chamber.

The above summary is not intended to describe each embodiment or every implementation possible. Rather, a more complete understanding of various illustrative embodiments will become apparent and appreciated by reference to the following Detailed Description of Exemplary Embodiments and claims in view of the accompanying figures of the drawing.

BRIEF DESCRIPTION OF THE VIEWS OF THE DRAWING

Exemplary embodiments will be further described with reference to the figures of the drawing, wherein:

FIG. 3 is an exploded perspective view of portions of the apparatus of FIG. 1;

FIGS. 9A-9G illustrate mufflers (each with one half removed) in accordance with alternative embodiments of the present disclosure, wherein: FIG. 9A illustrates a muffler baffle configuration similar to that shown in FIG. 8; FIG. 9B illustrates a baffle configuration using both chevrons and planar baffle segments; FIG. 9C illustrates a baffle configuration using only planar baffle segments; FIG. 9D illustrates a baffle configuration using discontinuous planar baffle segments or planar baffle segments having apertures formed therethrough; FIG. 9E illustrates a baffle configuration using serpentine baffle segments; FIG. 9F illustrates a baffle configuration using planar baffle segments orthogonal to flow; and FIG. 9G illustrates another baffle configuration using both chevron baffles and planar baffle segments;

FIGS. 10A-10D illustrate various methods for securing two muffler halves to one another, wherein: FIG. 10A illustrates snap-fit engagement; FIG. 10B illustrates a U-joint seal; FIG. 10C illustrates an ultrasonic weld configuration; and FIG. 10D illustrates a single muffler half showing an alternative snap-fit engagement configuration;

FIGS. 14A-14B illustrate yet another muffler configuration in accordance with embodiments of the present disclosure, wherein: FIG. 14A is a top view of the muffler with one half removed; and FIG. 14B is a perspective view thereof; and FIGS. 15A-15B illustrate still another muffler configuration in accordance with embodiments of the present disclosure, wherein: FIG. 15A is a top view of the muffler with one half removed; and FIG. 15B is a perspective view thereof.

Figure 1:
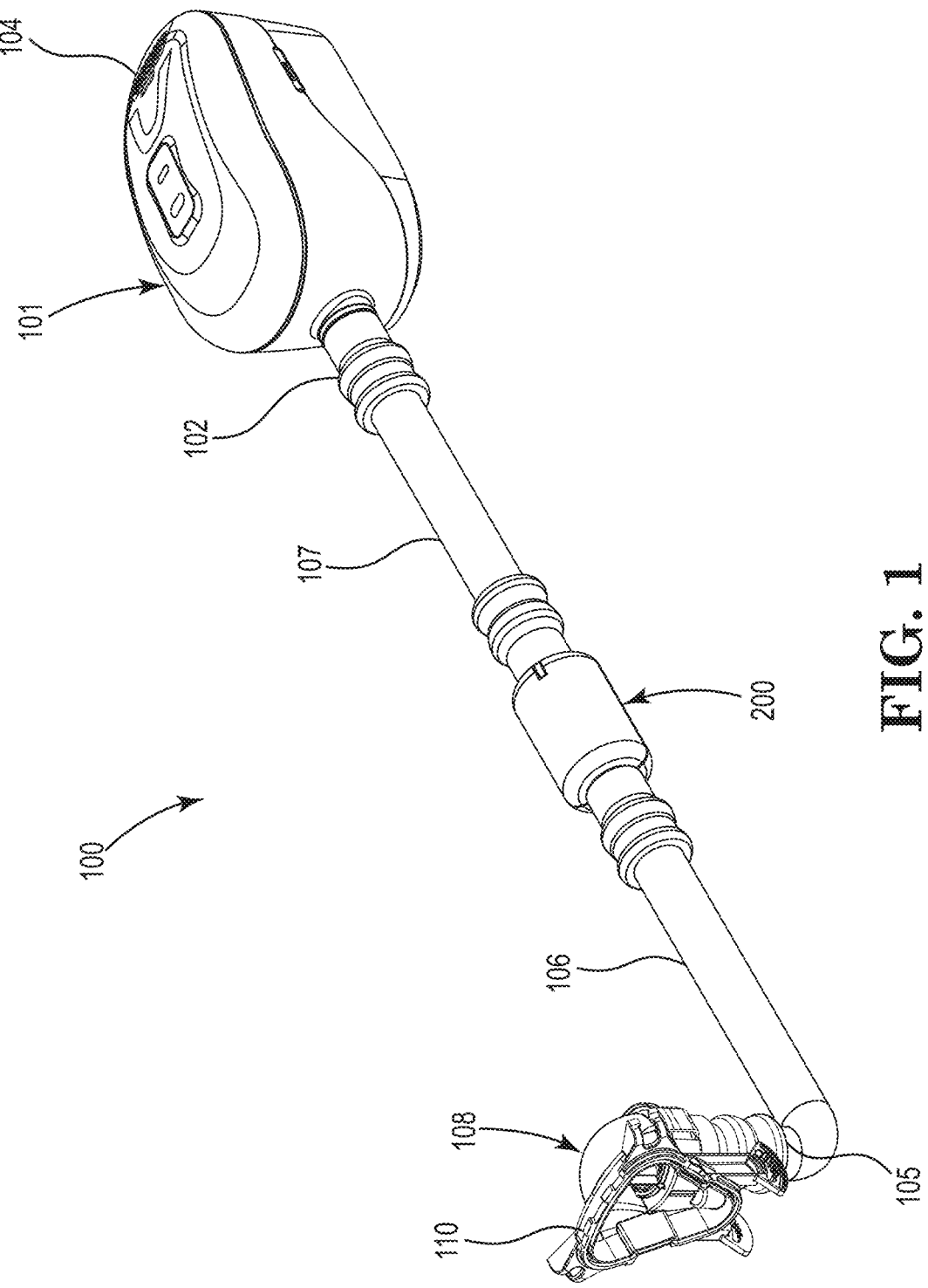
FIG. 1 is a perspective view of a positive airway pressure apparatus including an inline muffler in accordance with embodiments of the present disclosure, the muffler located between a blower and a user interface (e.g., mask)

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments. The lack of illustration/description of such structure/components in a particular figure is, however, not to be interpreted as limiting the scope of any embodiment in any way.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments that may be practiced.

Embodiments described herein are directed generally to positive airway pressure apparatus, systems, and methods and, more particularly, to inline mufflers for use with the same. While described herein primarily in the context of treatment of sleep-disordered breathing, those of skill in the art will realize that the same or similar embodiments are applicable to most any assisted respiration or ventilation system, and in fact to most any positive airway pressure apparatus/system. Variations, combinations, and modifications of the embodiments described herein will be apparent to those skilled in the art, and it should be understood that this disclosure is not limited to the illustrative embodiments set forth herein.

All headings provided are for the convenience of the reader and should not be used to limit the meaning of any text that follows the heading, unless so specified. Moreover, unless otherwise indicated, all numbers expressing quantities, and all terms expressing direction/orientation (e.g., vertical, horizontal, parallel, perpendicular, etc.) in the specification and claims are to be understood as being modified by the term "about." The term "and/or" (if used) means one or all of the listed elements or a combination of any two or more of the listed elements. The term "i.e." is used as an abbreviation for the Latin phrase id est and means "that is." The term "e.g." is used as an abbreviation for the Latin phrase exempli gratia and means "for example."

It is noted that the terms "have," "include," "comprise," and variations thereof, do not have a limiting meaning, and are used in their open-ended sense to generally mean "including, but not limited to," where the terms appear in the accompanying description and claims. Further, "a," "an," "the," "at least one," and "one or more" are used interchangeably herein. Moreover, relative terms such as "left," "right," "front," "fore," "forward," "rear," "aft," "rearward," "top," "bottom," "side," "upper," "lower," "above," "below," "horizontal," "vertical," and the like may be used herein and, if so, are for the benefit of explanation and/or are from the perspective shown in the particular figure. These terms are used only to simplify the description, however, and not to limit the interpretation of any embodiment described.

Figure 2:
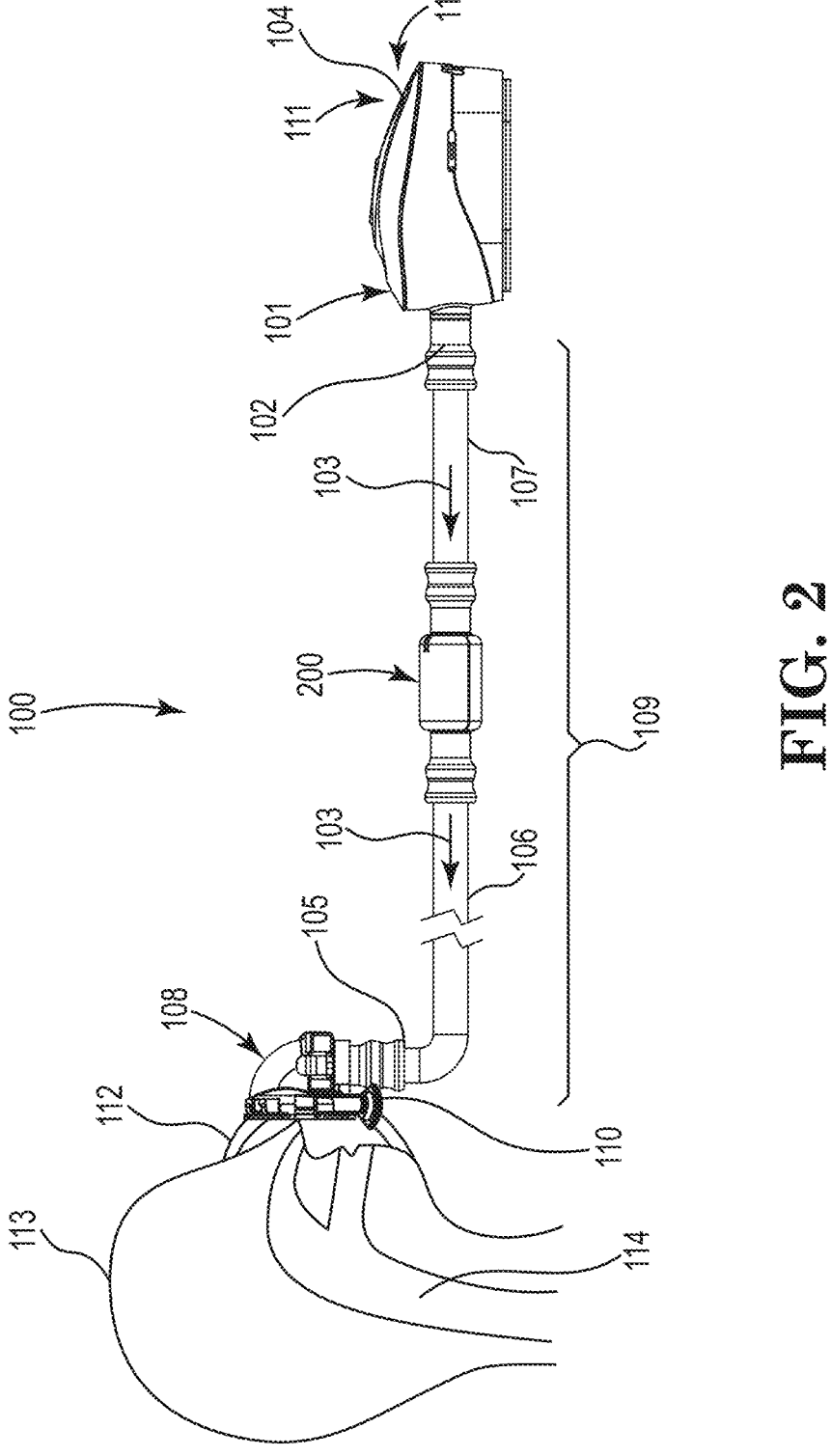
FIG. 2 is a side elevation view of the apparatus of FIG. 1.

With reference to the drawing, wherein like reference numerals designate like parts and assemblies throughout the several views, FIGS. 1 and 2 illustrate an exemplary, non-invasive, positive airway pressure (PAP) apparatus 100. The PAP apparatus 100 may include a flow generator forming a housing containing a blower 101 adapted to generate or otherwise produce a flow of pressurized gas 103 at a blower outlet 102. The outlet 102 is operatively coupled to and in fluid communication with a first or proximal end of an elongate delivery hose or tube 106 (via an intermediate hose 107 and muffler 200 as described below). A second or distal end of the tube 106 may be connected to an inlet 105 of a user interface 108. The user interface 108 may include a frame 110 adapted to support a flexible seal 112 (not shown in FIG. 1 but shown diagrammatically in FIG. 2). The user interface 108 may include most any structure that seals effectively to a user 113 (e.g., to the user's face) in such a way that pressurized gas delivered to the user interface may be communicated to an airway 114 of the user without excessive unintentional gas leakage. For example, the user interface could be a face mask that covers one or both of the user's mouth and nose; a nares pillow seal; an intubation tube; or any similar device. For simplicity, the user interface may be referred to herein simply as a "mask" 108 without limitation.

As used herein, the terms "air," "gas," and "fluid" are understood to include most any gas or gas-vapor combination. For example, the gas provided by the blower may include ambient air, oxygen, water vapor, medicinal vapor, and combinations thereof. For simplicity, the terms air, fluid, and gas may, unless otherwise indicated, be used interchangeably herein without limitation.

The tube 106 and user interface 108 may together define a portion of a gas delivery path or delivery conduit 109 (see FIG. 2) adapted to provide or communicate a flow of pressurized gas from the blower 101 to the airway 114 of the user 113. The delivery conduit 109 may include one or more vents or ports to provide what is referred to as an "intentional leak" or "intentional vent leak." The intentional leak may assist in purging carbon dioxide from the system during expiration to minimize the volume of carbon dioxide that may be re-breathed.

To produce the desired flow of pressurized gas 103 within the delivery conduit 109, the blower 101 may include a blower housing forming a volute containing an impeller or fan. An electric motor, such as a brushless DC motor, may couple to and rotate the fan. As the fan rotates, it draws gas (e.g., ambient air 111) in via an air inlet 104 of the blower housing where it is then compressed by the fan and expelled through the outlet 102 as a flow of pressurized gas 103. By controlling the rotational speed of the fan, the pressure of the flow of pressurized gas 103 within the delivery conduit 109 may be controlled to provide the desired treatment pressure to the user.

The apparatus 100 (e.g., the blower 101) may further include an electronic (e.g., microprocessor-based) controller that may, among other tasks, modulate or otherwise control a speed of the motor (and, accordingly, a speed of the fan), thereby regulating the treatment pressure and flow rate of the flow of pressurized gas 103. The controller and other components of the apparatus 100 may be powered by either an onboard power supply (e.g., a battery) or a remote power supply (e.g., AC or DC source).

While described and illustrated as a fan-based blower, the term "blower," as used herein, may include any device capable to delivering pressurized gas to the delivery conduit. For example, the blower could also be a tank or bottle of compressed gas that is metered by a valve to provide the appropriate pressure and flow.

During operation of the apparatus 100, acoustic noise (sound energy (i.e., pressure) travelling as waves through air or other gases) produced by the blower 101 and the resulting flow of pressurized gas produced thereby may propagate through and along the delivery conduit 109. This acoustic noise may be bothersome to some users and, for certain users, may even interfere with the ability to sleep. The terms "acoustic noise," "noise," and "sound," may be used interchangeably herein.

To address this issue, a muffler 200 defined by a tubular member or housing in accordance with embodiments of the present disclosure may be provided. As shown in FIGS. 1 and 2, the muffler may be an inline muffler that is operatively positioned between the blower 101 and the user interface 108. For example, as shown in FIGS. 1 and 2, the muffler 200 may be positioned in the gas delivery path between the blower 101 and the delivery tube 106.

Broadly speaking, the muffler 200 may define an expansion chamber within the delivery conduit 109. The muffler/expansion chamber may provide baffles (e.g., inwardly extending baffles) adapted to attenuate noise associated with the flow of pressurized gas as the gas passes through the muffler (such noise that would otherwise be detected downstream at the user interface). To achieve such noise attenuation, the baffles may be adapted to effectively capture sound waves (also referred to herein as sound energy or acoustic energy) associated with the flow of pressurized gas as the gas moves through the expansion chamber. As used herein, "capture" of sound energy may include most any baffle geometry that results in one or more of: destructive interference of sound energy; diffusion of sound energy; attenuation of sound energy; suppression of sound energy; absorption of sound energy; and redirection of sound energy. Mufflers in accordance with embodiments of the present disclosure may provide this capture function by configuring the baffles to interact with the flow of pressurized gas (as the gas passes through the expansion chamber) as described herein. As used herein, sound energy associated with the flow of pressurized gas may include sound energy produced: by the flow of gas; by the blower; and by any other system components that introduce acoustic energy into the system upstream of the muffler.

As stated above and shown in FIGS. 2-3, the muffler 200 may be operatively located between the blower 101 and the delivery tube 106. For example, the muffler housing may include a first end defining an inlet port 202 adapted to operatively couple to the blower outlet 102 (e.g., via an intermediate tubular hose 107), and a second end defining an outlet port 204 adapted to operatively couple to the proximal end of the delivery tube 106 that fluidly communicates with the user interface. The blower 101, hose 107, muffler 200, tube 106, and user interface 108 may be adapted to connect to one another as shown (see, e.g., FIG. 2) in a generally leak-free manner (other than any intentional leak provided on any one or more of these components).

Figure 4:
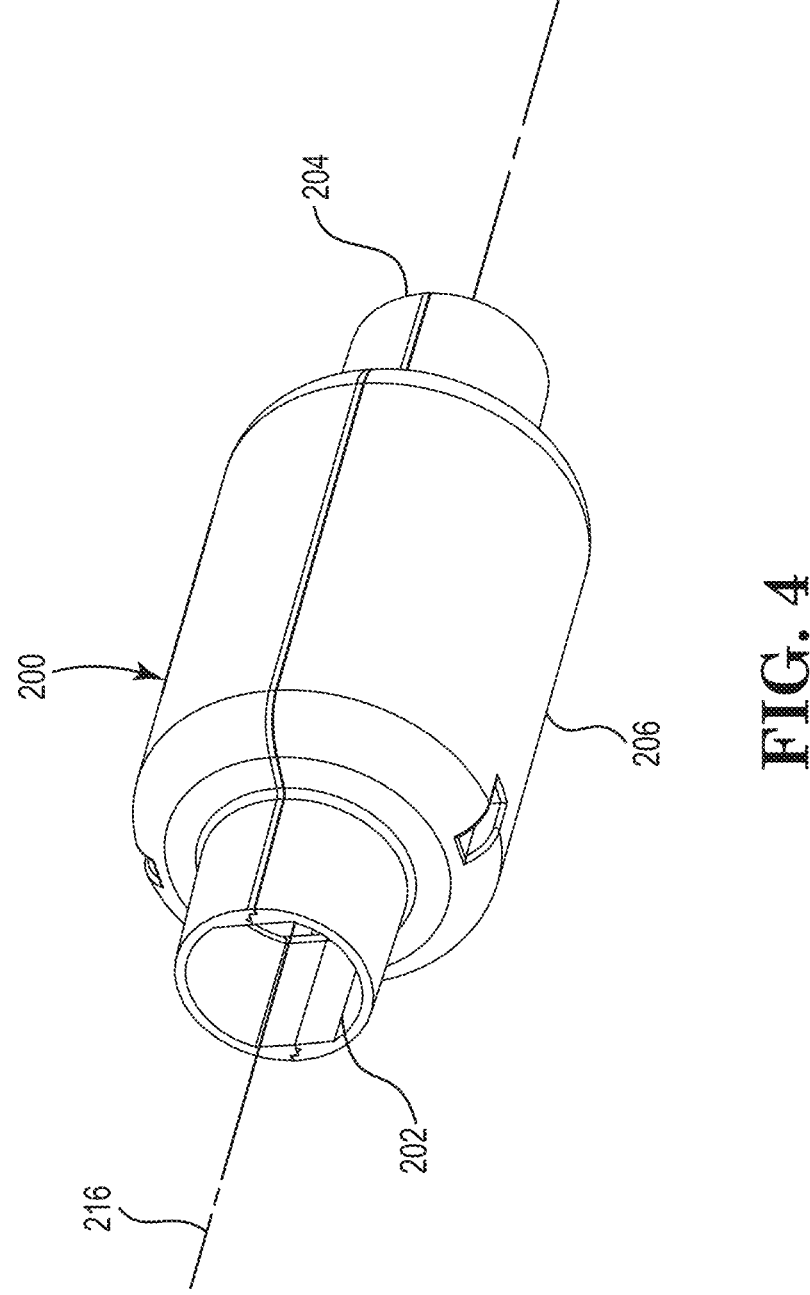
FIG. 4 is an isolated perspective view of the muffler of FIGS. 1-3.
Figure 5:
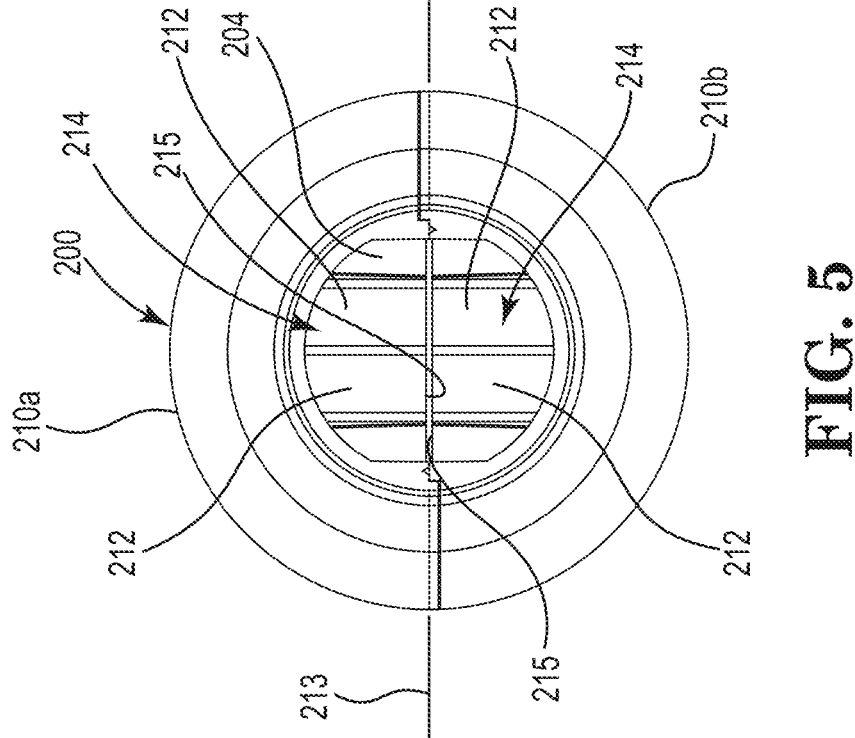
FIG. 5 is an end view of the muffler of FIG. 4.
Figure 6:
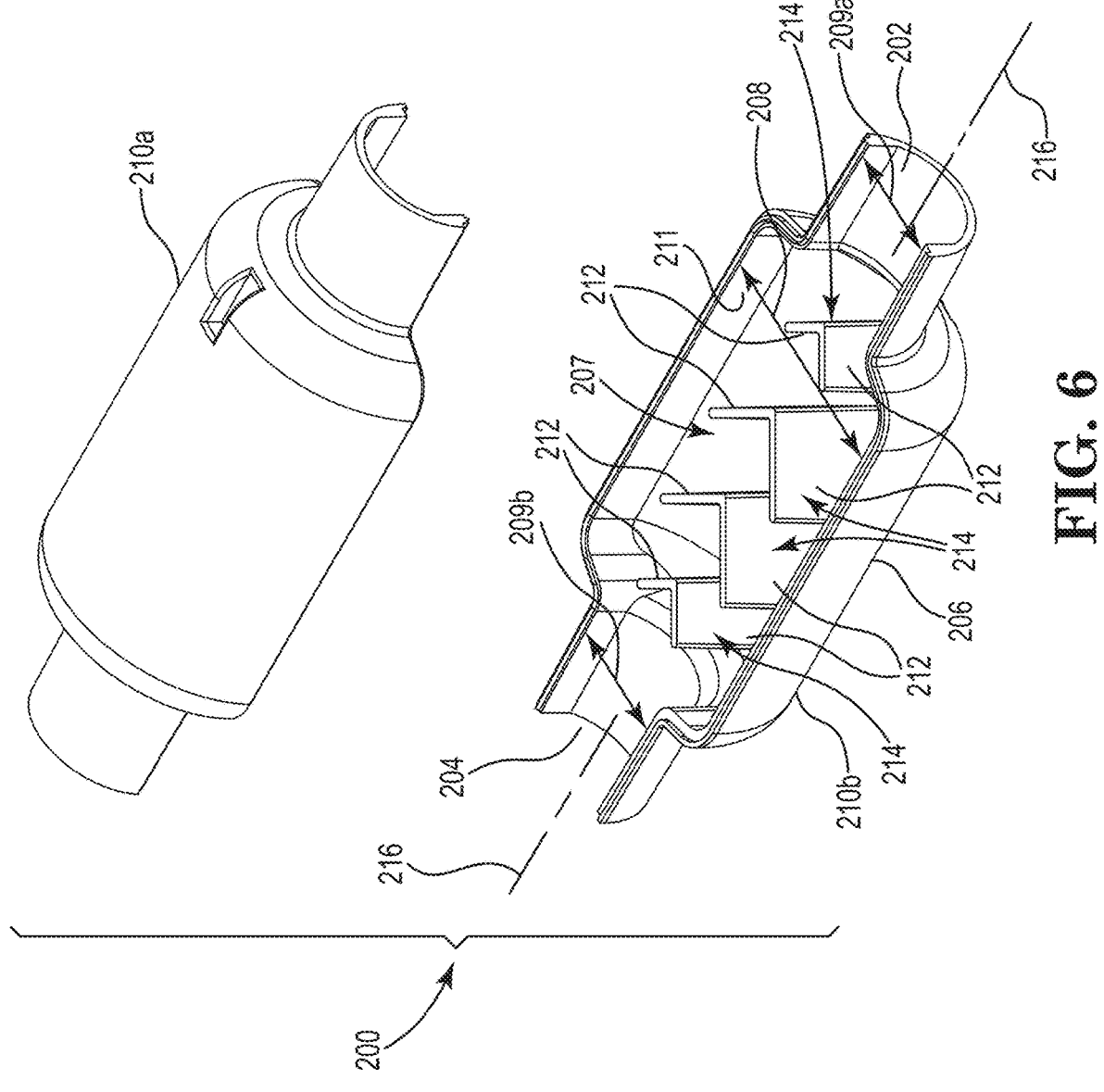
FIG. 6 is an exploded view of the muffler of FIG. 4.

FIG. 4 is an enlarged perspective view of the exemplary muffler 200, while FIGS. 5 and 6 illustrate an end view and an exploded view, respectively. As shown in these views, the inlet and outlet ports 202, 204 may define a muffler axis 216 generally coaxial with a flow axis of the delivery conduit 109. Moreover, the muffler 200/muffler housing may include a body 206 extending between the first and second ends (e.g., between the inlet and outlet ports 202, 204), wherein the body defines an expansion chamber 207 (see FIG. 6) also located between the first and second ends of the housing. The expansion chamber 207 may include an effective cross-sectional area (e.g., as defined by an effective inner diameter 208) larger than an effective cross-sectional area of both the inlet port 202 (as defined by inner diameter 209*a*) and the outlet port 204 (as defined by inner diameter 209*b*). Moreover, in some embodiments, baffles may extend from opposing inner walls of the expansion chamber. That is to say, an inner wall 211 of the body 206 (within the expansion chamber 207) includes a plurality of inwardly extending baffles (e.g., fixed baffles), the baffles adapted to capture sound energy associated at least with the flow of pressurized gas passing through the expansion chamber (e.g., passing from the inlet port to the outlet port of the muffler/muffler housing) by disrupting the flow of pressurized gas as further described below.

While referred to herein as "diameter" and "effective diameter," the inlet port 202, outlet port 204, and expansion chamber 207 may have most any cross-sectional internal (and external) shape without departing from the scope of this disclosure. That is to say, these terms may be used to refer to most any dimension associated with a cross-sectional geometry whether such geometry is circular or not. For example, the term "diameter" may be used to refer to a polygonal cross-sectional dimension, or an elliptical, oblong, or obround cross-sectional dimension without departing from the scope of this disclosure.

With reference still to FIG. 6, the exemplary muffler 200 (e.g., the muffler housing) may include or be defined by two symmetric halves 210*a*, 210*b* (referred to individually and collectively as half or halves 210), each half (and thus each baffle) being formed via a plastic (or other impermeable material), injection molding process. As each part is identical, the muffler 200 may yield manufacturing economies as compared to alternative constructions. The two halves 210 may be adapted to join or secure with one another along a generally planar mating surface 213 (see FIG. 5). Note that the actual mating surface may comprise stepped or curved surfaces, in which case the mating "surface" or mating "plane" may refer to a virtual or construction plane or surface about which the halves are symmetric when assembled. In other embodiments the two halves 210 may be symmetric in most pertinent respects yet may include different mating surface 213 configurations. Such variation in the mating surfaces 213 of the two halves 210 may, for example, assist with joining (e.g., ultrasonic welding of) the two halves to one another to form the muffler 200. However, even with these mating surface variations, most or all other aspects of the halves—e.g., the expansion chamber 207, the baffles 214, baffle segments 212, etc. that provide the majority of the acoustic noise capture function as described below—may be symmetric. Accordingly, as used herein with respect to describing the halves 210, "symmetric" and like terms refer to structural symmetry of those features and components of the two halves that provide the primary acoustic noise capture mechanism and not necessarily those aspects related to joining the two halves to one another.

As shown in FIG. 6, each of the halves 210 may include one or more baffles 214 each formed by one or more baffle segments 212 extending into the expansion chamber 207, e.g., from the inner wall 211 thereof. Due to the symmetry of the halves 210 (e.g., of the baffle segments), each baffle segment 212 of the half 210a may align with a corresponding baffle segment 212 of the half 210b (near and along the mating plane) to form a mostly continuous baffle 214 (see FIG. 5) extending across the expansion chamber 207 when the halves are assembled (in reality, a small gap may exist between two corresponding elements as indicated in FIG. 5.) Each half 210 may include multiple baffle segments 212 positioned along the muffler axis such that the baffles 214 interfere or capture acoustic (sound) energy propagating through the expansion chamber.

The term "baffle" may be used herein to identify the baffle components associated with each of the halves 210, as well as to identify the combined baffle resulting from assembly of the two halves 210 (e.g., in FIG. 5, baffle 214 identifies both the portion of the baffle associated with half 210a and the portion associated with the half 210b, as well as the resulting complete baffle produced when the two halves are assembled as shown). Similarly, the term baffle "segment" or "element" may refer to the segments 212 associated with each of the halves 210 (as shown in FIG. 6) as well as to the complete segments spanning across the expansion chamber resulting from assembly of the two halves 210 (see FIG. 5).

Figure 7:
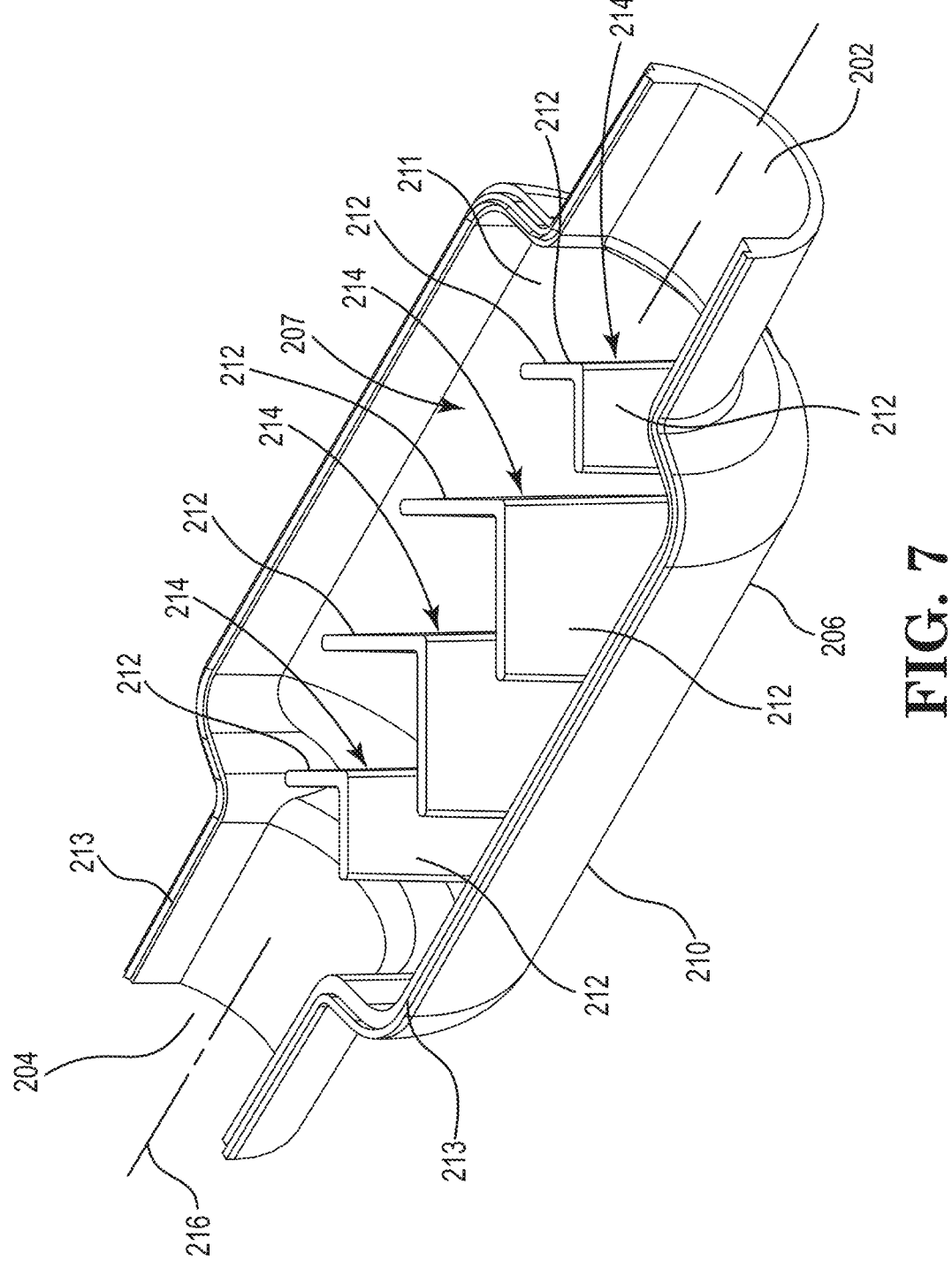
FIG. 7 is a perspective view of one half of the muffler of FIG. 4.

FIG. 7 is an enlarged perspective view of an isolated half 210 of the muffler 200 illustrating an exemplary baffle/baffle segment structure. As shown in this view, one or more of the baffles 214 may be configured as two intersecting planar baffle segments 212 such that each baffle 214 defines a chevron or chevron baffle 214 when viewed normal to the mating surface 213. Moreover, as shown in this view, the two intersecting planar baffle segments 212 that form each chevron baffle 214 may intersect one another along a line that also intersects the muffler axis 216.

As stated above, one or more of the baffles 214/baffle segments 212 may extend inwardly from the inner wall 211 as shown. In some embodiments, the baffles 214/baffle segments are integrally formed (e.g., molded) with the body of the muffler 200 (e.g., with the inner wall) and extend from the inner wall orthogonally toward, and terminating at or near, the plane defined by the mating surface 213 (see, e.g., FIG. 5). That is to say, corresponding baffle segments of each half 210 may include distal portions that terminate at or near one another within the expansion chamber. As a result, when the two halves 210 are assembled, the baffle segments 212 of each half extend generally from the inner wall 211 to a distal end 215 proximate a distal end 215 of the corresponding baffle segment 212 of the opposing half. As stated above, these two baffle segments combine to form a larger baffle segment as shown.

Figure 8:
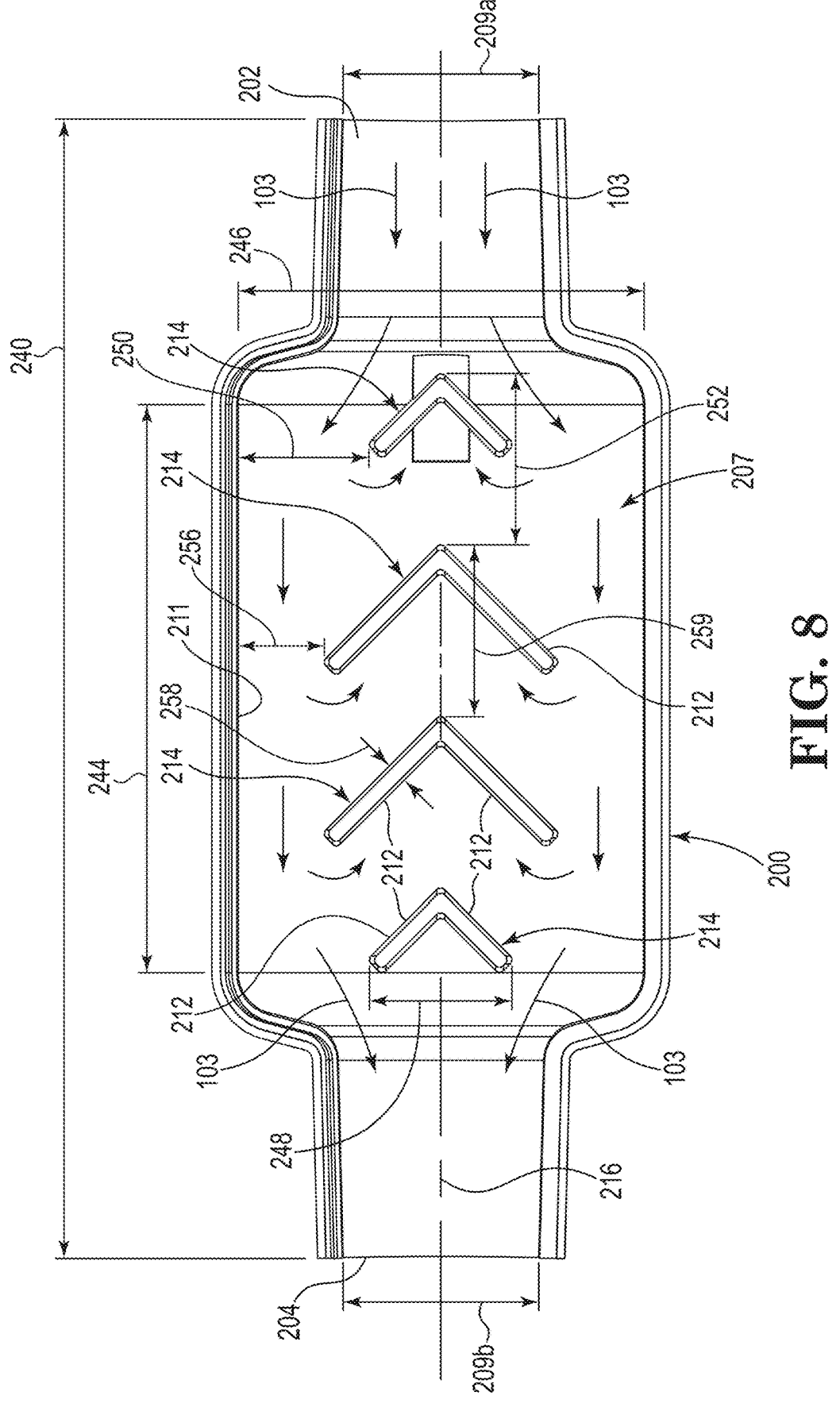
FIG. 8 is a top plan view of the muffler half of FIG. 7.

In the exemplary muffler 200 shown in FIG. 8, the chevron baffle 214 proximate each end of the expansion chamber may be smaller than the chevron baffles positioned between. For example, the end baffles 214 may have a width 248 of 12 millimeters (mm) such that each corresponding segment or baffle "leg" is spaced apart from the inner wall 211 by a distance 250 of 12 mm. Each end baffle 214 may be spaced (along the muffler axis 216) from its proximate intermediate baffle by a distance 252 of 15 mm, while each intermediate baffle 214 may be spaced from each other by a distance 259 of 15 mm. As indicated in FIG. 8, the intermediate chevron baffles 214 are larger such that the planar baffle segments 212 of each are spaced apart from the inner wall 211 by a distance 256 of 8 mm. Each of the four chevron baffles 214 may have a thickness 258 of 1.8 mm.

While other configurations are certainly possible, the muffler 200 may have: an overall length 240 of 100 mm; a diameter 209a of the inlet port 202 and diameter 209b of the outlet port 204 of 17 mm; an expansion chamber length 244 of 50 mm; and an expansion chamber diameter 246 of 36 mm. While shown as being generally equivalent, the diameters 209a and 209b and the relative shapes and sizes of the inlet port 202 and outlet port 204 could be different from one another to, for example, permit installation of the muffler in only one flow direction. The four, 90-degree chevron baffles 214 are oriented symmetrically relative to the muffler axis 216 (i.e., having apexes that intersect (and are centered along) the muffler axis) as shown such that planar baffle segments 212 of each of the chevron baffles 214 extend at an angle of 45 degrees to the muffler axis. All of the chevron baffles may converge toward (i.e., point to) the muffler inlet as shown.

FIG. 8 further illustrates an exemplary flow of pressurized gas (as represented by arrows 103) as it enters the inlet port 202, travels through the expansion chamber 207, and exits the outlet port 204. As indicated in this view, as the gas enters the expansion chamber, it is re-directed from its primarily axial direction via interaction with the chevron baffles 214. This disruption of gas flow may effectively reduce the acoustic noise detected downstream of the muffler (e.g., at the user interface 108 (see FIG. 2)) associated with operation of the blower by capture of sound energy. The actual gas flow patterns and sound pressure energy may vary depending on such factors as baffle geometry, e.g., length and diameter of expansion chamber and inlet and outlet ports, number of baffles, gas pathway size, etc.

While shown utilizing a particular baffle geometry in FIG. 8, such a configuration is exemplary only. That is other baffle geometries are also contemplated. For example, FIGS. 9A-9G illustrate mufflers having various baffle geometries (each view having one muffler half removed to illustrate the baffle construction), wherein FIG. 9A shows a chevron baffle geometry similar to that shown in FIGS. 6-8. FIG. 9B shows a discontinuous baffle geometry, wherein separate spaced-apart baffle segments 212-1 and 212-2 may allow gas to pass through openings 217 therebetween. In alternate embodiments, the baffle segments 212-1 and 212-2 may be a singular baffle segment wherein the openings 217 are formed by apertures through the baffle segments. In FIG. 9C, the baffle segments 212-3 are shown offset from the muffler axis 216, while FIG. 9D illustrates a similar baffle construction with perforations or apertures formed therein (or alternatively separate, spaced-apart baffle segments 212-4, 212-5 to produce the opening 217). FIG. 9E illustrates a muffler wherein the baffle segments 212-6 are constructed as curved or serpentine, as opposed to planar, elements. While the planar elements of FIGS. 9A-9D each define a plane that intersects the muffler axis 216 at oblique angles, FIG. 9F illustrate a series of offset planar baffle segments 212-7 that are oriented orthogonally to the axis 216, while FIG. 9G illustrates baffle segments 212-8 defining chevrons and planar baffle segments 212-9 oriented at various angles throughout the expansion chamber. As one can appreciate, other baffle configurations are certainly possible. In fact, most any baffle configuration that effectively disrupts the flow of pressurized gas within the expansion chamber is contemplated.

While some of these baffle configurations are clearly bi-directional (see, e.g., FIGS. 9E, 9F, and 9G), others may be optimized for flow in a single direction. However, even with the latter constructions, sound capture (e.g., sound-attenuating) benefits may be realized even when flow is reversed. That is to say, while some muffler constructions may be designed for unidirectional operation (i.e., a designated inlet port and designated outlet port), they may also provide benefits even when the flow direction is reversed.

Figures 10A, 10B, 10C, 10D:
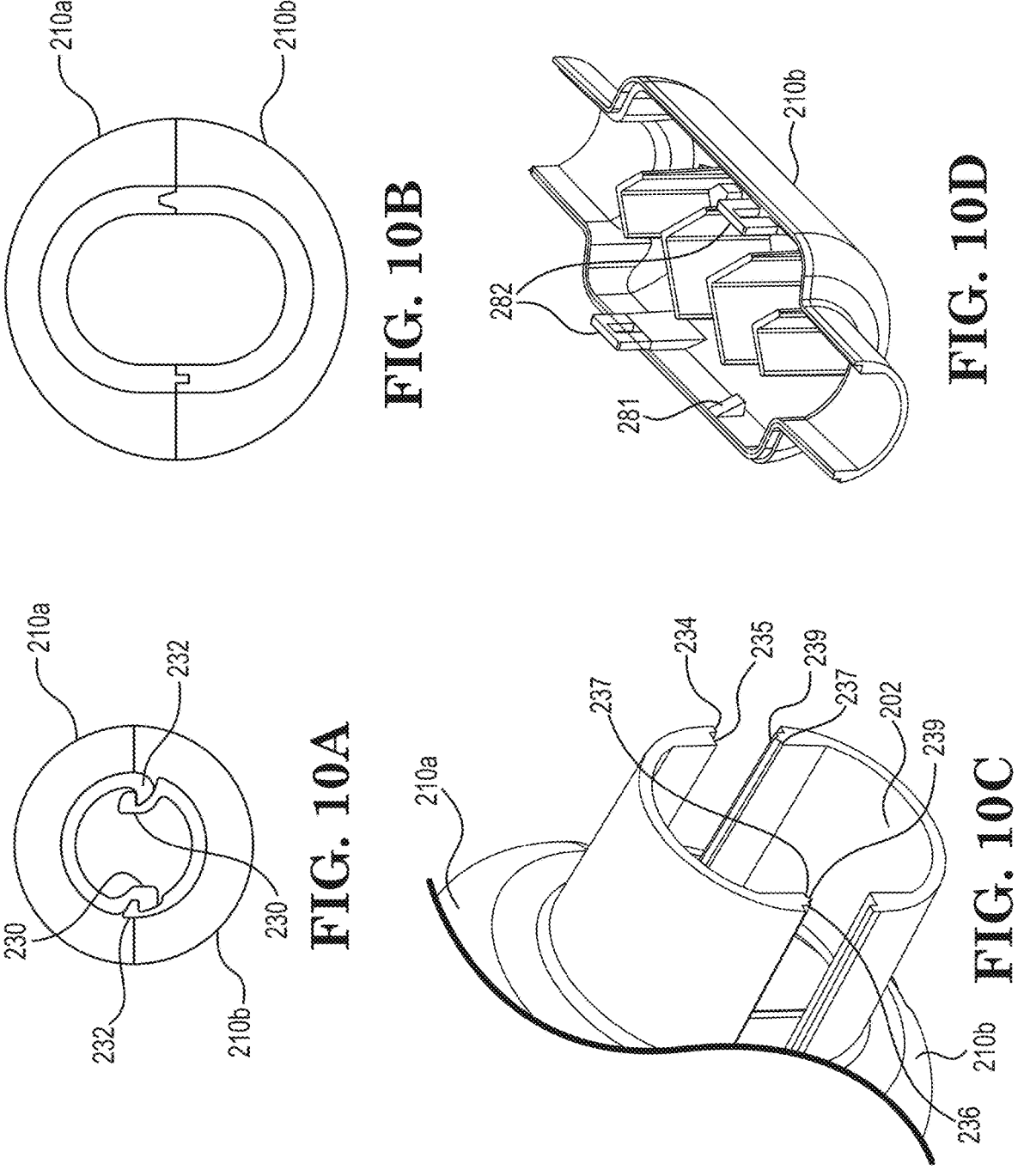

Regardless of the baffle configuration, the halves 210 may be secured via any acceptable process. For example, the halves may be secured via snap-fit engagement as shown in FIG. 10A. As used herein, "snap-fit" refers to the coupling of flexible parts to one another by deflection of an interlocking element of one part as it engages an associated element of the other part, after which the deflected part returns to its undeflected position. FIG. 10A illustrates each half 210 having interlocking ears 230, 232 adapted to engage ears 232, 230 of the opposing half. FIG. 10D illustrates an alternative snap-fit engagement configuration (only half 210b shown). Wherein the ears 232, 230 shown in the embodiment of FIG. 10A may run along most or all of the edges of the halves 210a, 210b, the embodiment of FIG. 10D may utilize discrete snap-fit components (e.g., tabs 281 (only tab on one side of half 210b being visible) and latches 282). The embodiment of FIG. 10D may offer various advantages over the embodiment of FIG. 10A, e.g., simplified manufacturing/assembly. While shown with a tab 281 and latch 282 along each transverse edge of the half 210b (or 210a), other embodiments may differ (e.g., multiple tabs on one transverse edge, with multiple latches on the other).

In other embodiments, the halves 210 may be secured using a step joint or U-joint seal, the later shown in FIG. 10B. Other embodiments may alternatively or in addition, join the halves using: fasteners (e.g., threaded fasteners); dowel pins; rivets; and bonding agents (e.g., epoxy, silicone, adhesive). In still other embodiments, the halves may be secured to one another via an overmolding process. While not illustrated, any of the joining processes described herein may incorporate the use of a compressible seal (e.g., elastomeric seal) positioned between the halves to, for example, reduce air leakage.

In some embodiments, the halves 210 may be secured to one another via ultrasonic welding. For example, FIG. 10C is an enlarged view of the muffler 200 showing the inlet port 202 prior to ultrasonic welding of the two halves to one another. As is evident in this view, each half may have offset stepped surfaces 234, 235 along one mating edge, and offset surfaces 236, 237 along the other mating edge, wherein these surfaces effectively define the constructive mating surface of the two parts. For instance, the surfaces 234, 235 of each half may abut/engage surfaces, 236, 237, respectively, of the opposing half during assembly. As is known in the ultrasonic welding art, one surface (e.g., the surface 237)

may include an energy director 239 to assist with the welding operation. Moreover, in practice, the distal ends of the baffle segments 212 (see distal ends 215 in FIG. 5) of each half may terminate short of the corresponding baffle elements of the opposing half after assembly to, for example, minimize vibration damage during welding.

While not wishing to be bound to a particular material, mufflers in accordance with embodiments of the present disclosure may by constructed of plastic (such as high-density polyethylene (HDPE), low-density polyethylene (LDPE), acrylonitrile butadiene styrene (ABS), polycarbonate (PC), blends of multiple materials (e.g., ABS/PC blends), polypropylene (PP), or other rigid or semi-rigid injection molded materials). Such plastics are beneficial not only due to their suitability for injection molding, but also because of their impermeability characteristics. As a result, exemplary mufflers constructed of such plastics may be easily cleaned after use and may even be used in conjunction with humidified PAP apparatus.

EXAMPLES

Figures 11, 12:
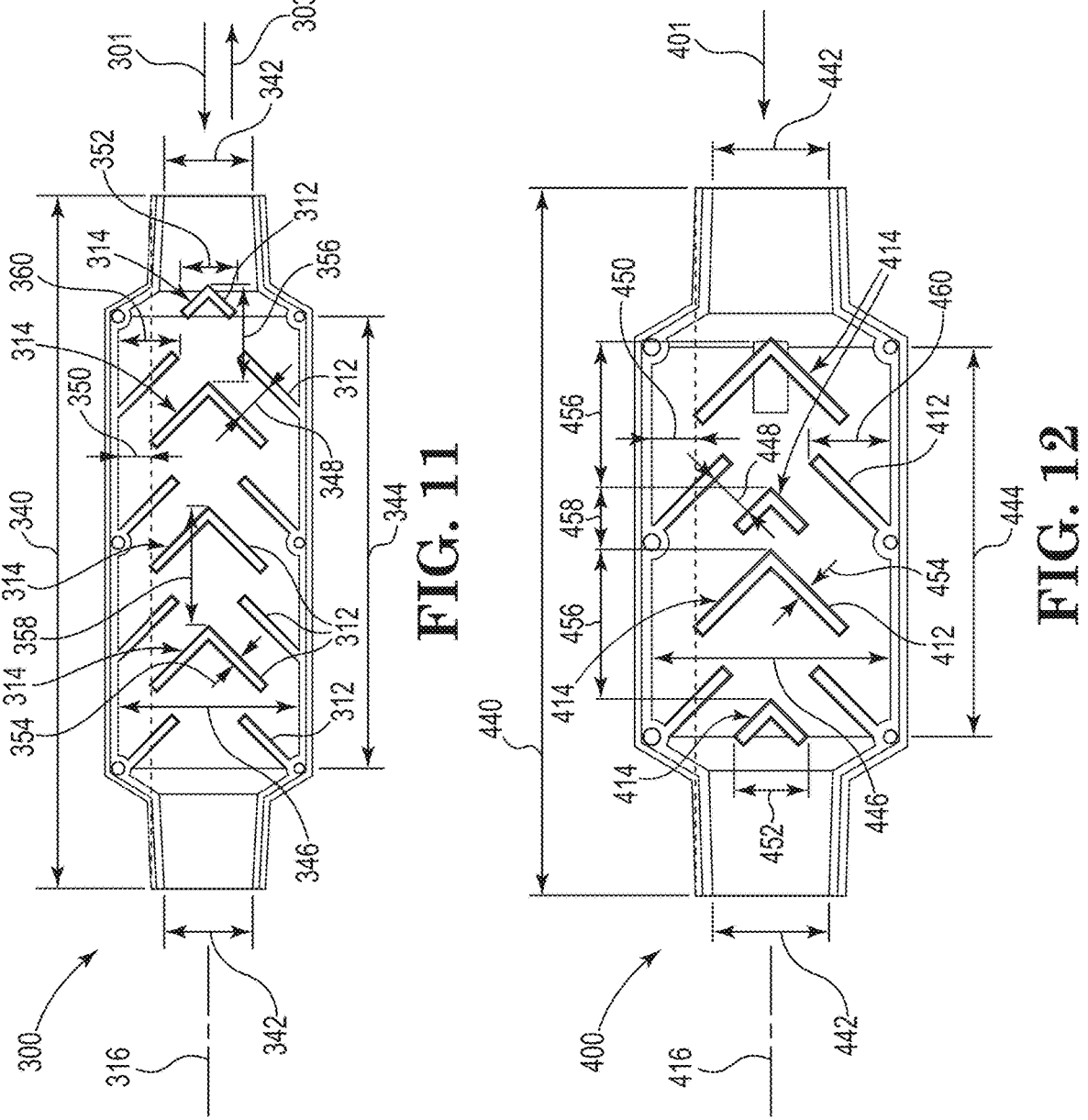
FIG. 11 illustrates yet another muffler configuration (with one half removed) in accordance with embodiments of the present disclosure.
FIG. 12 illustrates still another muffler configuration (with one half removed) in accordance with embodiments of the present disclosure.

Two exemplary mufflers 300 and 400 are illustrated in FIGS. 11 and 12, respectively. The muffler 300 has: an overall length 340 of 134 millimeters (mm); a diameter 342 of the inlet port and outlet port of 17 mm; an expansion chamber length 344 of 87 mm; and an expansion chamber diameter 346 of 35 mm. Mufflers as described herein may further provide external inlet and outlet diameters adapted to accommodate standard respiratory components. For example, the external diameters of the inlet and outlet ports may be 22 mm as identified in International Organization for Standardization (ISO) 5356-1. That being said, the external diameters, as well as the other dimensions of the muffler 300, may be modified without departing from the scope of this disclosure.

The muffler 300 includes a series of four, 90-degree chevron baffles 314 (with one being smaller than the other three) each formed by pairs of planar baffle segments 312 having apexes that intersect the muffler axis 316 as shown, and eight lateral planar baffle segments 312 offset from the muffler axis as shown but oriented at the same angle as the chevron baffle segments (e.g., 45 degrees to the muffler axis 316 when viewed normal to the mating plane). The orthogonal offset 348 between various baffle segments is 7.7 mm, and the offset 350 of the larger planar baffle segments of each of the chevron baffles from the inner wall of the expansion chamber (when viewed normal to a mating plane of the two halves) is 6.4 mm.

As illustrated in FIG. 11, the chevron baffle 314 proximate the inlet may be smaller than the remaining baffles. Moreover, this smaller chevron baffle may be positioned at least partially outside of the expansion chamber as shown. In this exemplary embodiment, this initial (smaller) chevron baffle has a width 352 across the flow path of 10 mm, wherein a thickness 354 of all the planar baffle segments 312 is 1.5 mm. The larger chevron baffle 314 proximate the smaller chevron baffle may be spaced apart from the smaller chevron baffle (measured from their respective apexes along the muffler axis 316) by a distance 356 of 19 mm, while the larger chevron baffles are spaced from one another by a distance 358 of 23 mm. Finally, the lateral planar baffle segments each form a lateral baffle that may extend from the inner wall at a 45 degree angle to the muffler axis such that distal ends of the lateral planar baffle segments are spaced apart from the inner wall by a distance 360 of 10.5 mm.

Again, it is worthwhile to note that it is the overall geometry of the muffler that may ultimately dictate its effectiveness at noise capture. For example, the combination of the effective cross-sectional area of the gas pathways, the surface area of the walls forming the pathways (i.e., the wall/chevron effects on gas flow), and the sharpness of the "turns" created by the baffles may all impact the ability of the muffler to capture acoustic energy. Stated alternatively, there is a correlation between gas flow resistance and how effectively the muffler can capture acoustic energy from the flow of pressurized gas.

With reference now to FIG. 12, the muffler 400 has: an overall length 440 of 104 mm; a diameter 442 of the inlet port and outlet port of 17 mm; an expansion chamber length 444 of 57 mm; and an expansion chamber diameter 446 of 35 mm. The muffler 400 include a series of four, 90-degree chevron baffles 414 (with alternating sizes as shown) each formed by planar baffle segments 412 having apexes that again intersect the muffler axis 416 as shown, and four lateral planar baffle segments 412 offset from the muffler axis, but oriented at the same angle as the chevron baffle segments (e.g., 45 degrees to the muffler axis 416 when viewed normal to the mating plane). The orthogonal offset 448 between various baffle segments is 7 mm, and the offset 450 of the planar baffle segments of each of the chevron baffles from the inner wall of the expansion chamber (when viewed normal to the mating plane) is 6.5 mm.

As further illustrated in FIG. 12, the size of the chevron baffles 414 may alternate, such that the first and third chevron baffles (in the air flow direction 401) are larger than the second and fourth chevron baffles. In this exemplary embodiment, the (smaller) chevron baffles have a width 452 across the flow path of 10 mm, wherein a thickness 454 of all the planar baffle segments 412 is 1.5 mm. The distance 456 between the first and second chevron baffles—as well as the distance between the third and fourth chevron baffles (measured from their respective apexes along the muffler axis 416)—is 19 mm, while a distance 458 between the second and third chevron baffles is 9 mm. Finally, the lateral planar baffle segments 412 form lateral baffles that may extend from the inner wall at a 45 degree angle to the muffler axis 416 such that distal ends of the lateral planar baffle segments are spaced apart from the inner wall by a distance 460 of 12.5 mm.

Initial testing of the mufflers 300 and 400 was conducted using a configuration like that shown in FIG. 2, wherein the hose 107 had a length of 200 mm, and the tube 106 had a length of 1,220 mm. The user interface 108 was an "AirFit F20" full face mask seal sold by ResMed Inc. of San Diego, California, USA and was connected to a mannequin head. The PAP blower was a model "Transcend 3 miniCPAP Auto" continuous positive airway pressure (CPAP) device manufactured by Somnetics, International, Inc. of Fridley, Minnesota, USA. A microphone setup was arranged according to ISO 3744 section 7.2 (per ISO 80601-2-70) about the mannequin head and user interface. The mannequin head utilized an air flow system adapted to simulate user breaths. Table 1 below shows results of testing with: no muffler installed; with muffler 300 installed and with air flow direction 301; and with muffler 400 installed and with air flow direction 401. "Dynamic sound level" is the sound power level detected when running a sinusoidal breathing simulator with the associated tidal volume and breaths per minute as indicated in Table 1 for a total of 10 seconds, and then averaged over 3 runs.

TABLE 1

| Muffler Present | Blower Pressure, cm H$_2$O | Muffler Pressure Drop, cm H$_2$O | Tidal Volume, milliliters | Breaths/ minute | Dynamic Sound Level, dBA * | Delta, dBA * |
|---|---|---|---|---|---|---|
| None | 10 | N/A | 500 | 20 | 39.0 | NA |
| 300 | 10 | 0.29 | 500 | 20 | 36.8 | −2.2 |
| 400 | 10 | 0.19 | 500 | 20 | 37.5 | −1.5 |

* as measured in and around the user interface when the muffler was 105 +/− 5 centimeters from the mannequin head.

As shown from these data, the mufflers 300 and 400 produced a noticeable reduction in detected dynamic sound levels at the user interface. It was also observed that, at least with respect to the muffler 300, similar reductions in detected noise occurred when the air flow direction was reversed (e.g., air flow in direction 303). Accordingly, as stated above, even mufflers designed for installation in a particular direction may yield benefits when installed in reverse.

Similar testing was also conducted using muffler constructions generally similar to the muffler 200 of FIG. 8 and the muffler shown in FIG. 9G. While the realized noise capture levels were less than the reduction realized with the mufflers shown in Table 1 above, these alternative mufflers did produce smaller pressure drops.

Figure 13:
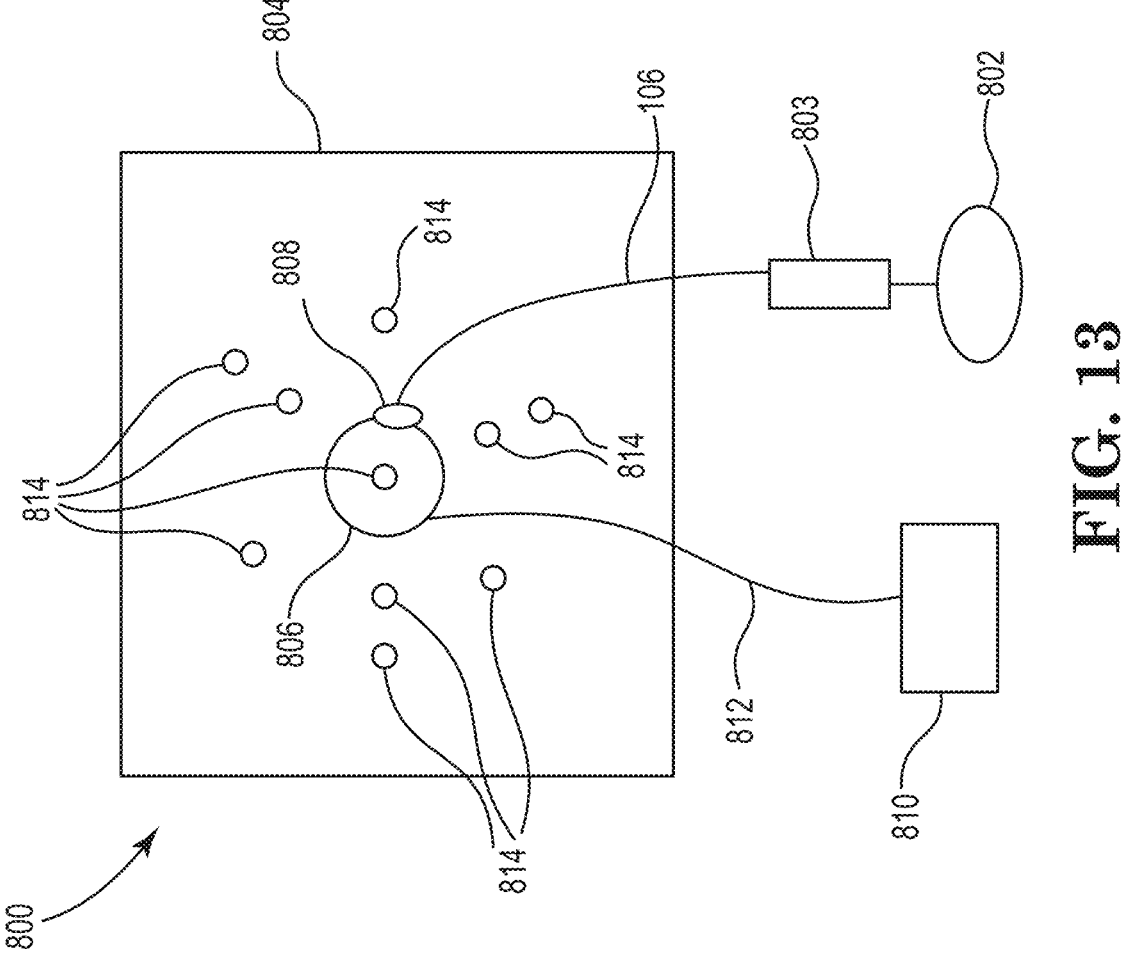
FIG. 13 is a block diagram of an exemplary testing configuration used to evaluate various mufflers.

FIG. 13 illustrates a specific example test setup 800 designed to evaluate sound power level reduction associated with various muffler configurations as further described below. This test setup was designed to better determine muffler performance by isolating the CPAP and then measuring the acoustic noise travelling along the delivery conduit (hose and mask), i.e., travelling through the muffler. In this exemplary setup, the CPAP device 802 (again, a model "Transcend 3 miniCPAP Auto" CPAP) and muffler 803 were located outside of an anechoic chamber 804, while an airway simulation mannequin 806 (as used herein, "mannequin" refers to a human head and neck mannequin such as a model LF03667U mannequin distributed by Nasco Education, LLC of Fort Atkinson, Wisconsin, USA) fitted with the AirFit F20 mask 808 was positioned within the chamber. As the CPAP device 802 and muffler 803—which may represent any of the mufflers shown and/or described herein—were located outside the chamber, sound power levels detected near the mannequin were generally limited to the sound energy propagating along the delivery conduit (e.g., hose 106 and mask 808). This setup was thus able to determine changes in sound power levels attributable to the use of a muffler such as those configured in accordance with exemplary embodiments of the present disclosure. The testing configuration and methods are consistent with those described in ISO 3744:2010.

As shown in FIG. 13, a breathing simulator 810 was also located outside of the chamber 804 and connected to an artificial airway of the mannequin 806 via a conduit 812. In this particular testing configuration, the mannequin 806 included artificial nasal, mouth, and tracheal passageways. Moreover, the mannequin 806 included facial features/structure mimicking a human face to accommodate typical fit of the mask 808.

The mannequin 806 was laid on a platform in a "face up" orientation to simulate a human sleeping in a supine position. The hose 812 was then connected to the mannequin's simulated tracheal airway or "windpipe" through connections in the "neck" of the mannequin.

To detect sound power levels, an array of microphones 814 was arranged upon a virtual hemispherical dome surrounding the mannequin 806. The array included a total of ten microphones, wherein the locations of the ten microphones were selected using microphone locations 1-10 as identified in ISO 3744:2010, Figure B.2. The virtual hemispherical dome had a one meter radius, wherein each microphone 814 was directed to a center of the hemispherical dome, the center of the dome generally coinciding with a geometric center of the head of the supine mannequin 806.

The breathing simulator 810 used was a model 17050 distributed by VacuMed of Ventura, California, USA and was configured to generate sinusoidal simulated breathing of 20 breaths/minute, each breath having a tidal volume of 500 milliliters. In this testing configuration, no mask leak was provided along the delivery conduit.

Figure 14A:
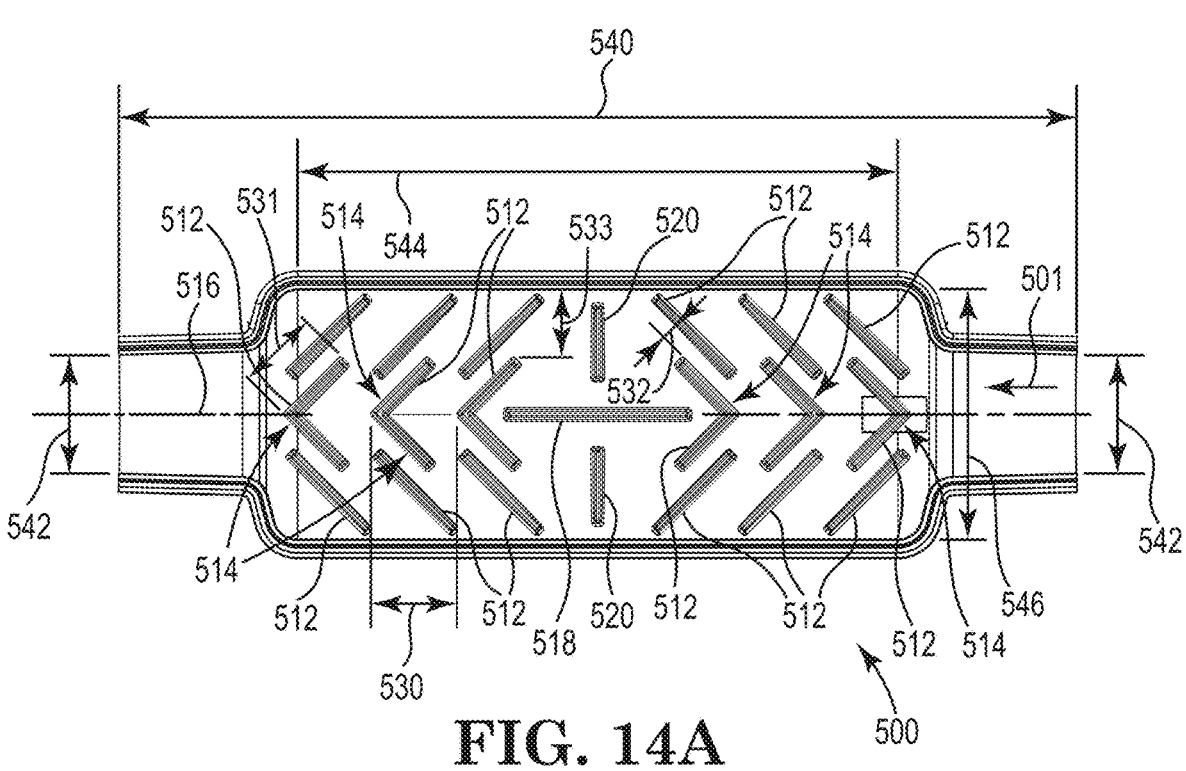
Figure 14B:
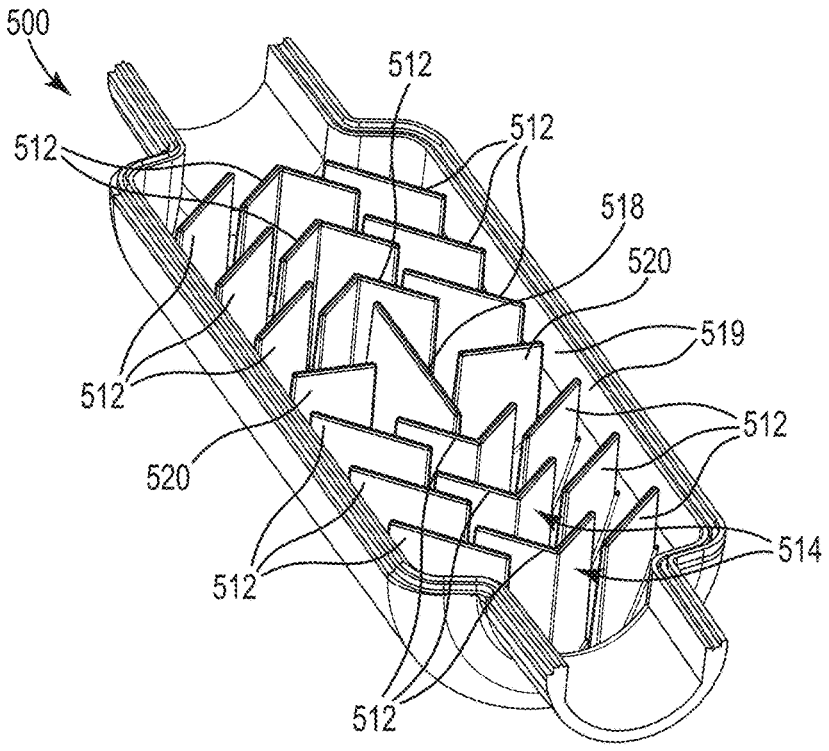
Figure 15A:
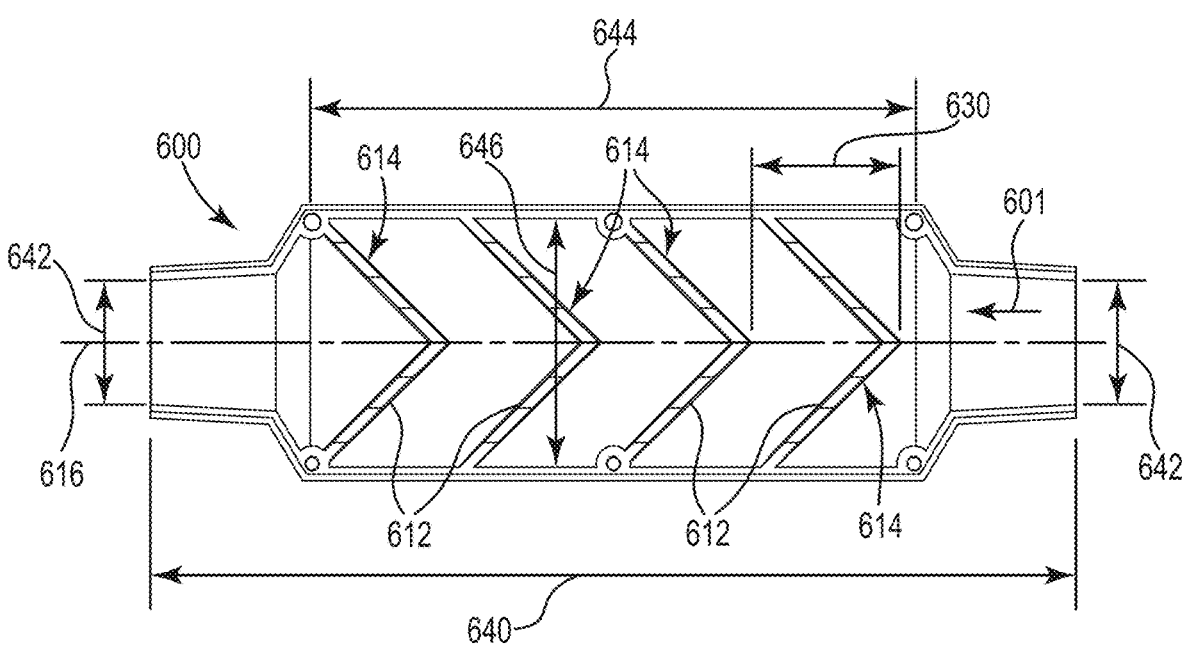
Figure 15B:
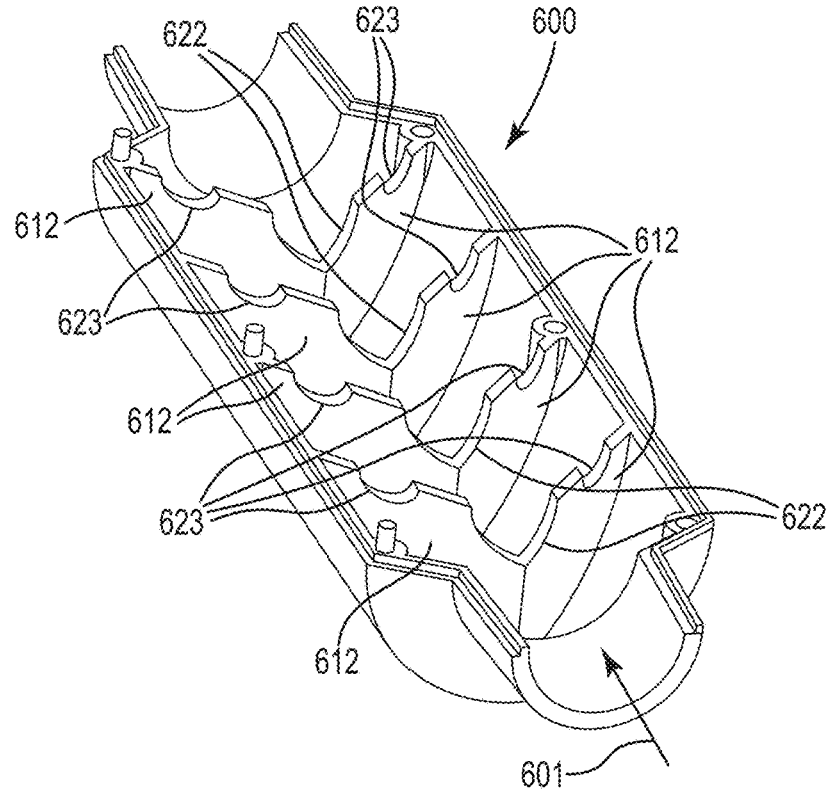

Using this configuration, tests were conducted with: no muffler; using the mufflers 200, 300, and 400 described herein; and using muffler 500 shown in FIGS. 14A and 14B and muffler 600 shown in FIGS. 15A and 15B. The mufflers 500 and 600 are now briefly described.

The muffler 500 illustrated in FIGS. 14A and 14B (singularly and collectively referred to herein as "FIG. 14") has: an overall length 540 of 134 mm; a diameter 542 of the inlet port and outlet port of 18 mm; an expansion chamber length 544 of 84 mm; and an expansion chamber diameter 546 of 35 mm. In this embodiment, the muffler included a series of six, 90-degree chevron baffles 514 each formed by two planar baffle segments ("legs") 512 oriented symmetrically relative to the muffler axis 516 (i.e., having apexes that intersect (and are centered along) the muffler axis) as shown such that the planar baffle segments 512 of each of the chevron baffles 514 extend at an angle of 45 degrees to the muffler axis 516. Three of the chevron baffles (those closest to the inlet) may converge toward (i.e., point to) the muffler inlet as show, and three (those closest to the outlet) may converge toward the muffler outlet.

The muffler 500 may further include 6 pairs (12 total) of lateral planar baffle segments 512 extending from near the inner wall of the expansion chamber toward, but terminating short of, the muffler axis. In the example shown in FIG. 14A, a lateral planar baffle segment 512 may be positioned proximate, and extend parallel with (at the same angle as), each of the planar baffle segments 512 of each chevron baffle. That is to say, each chevron baffle 514 may have a lateral planar baffle segment 512 associated with each of its planar baffle segments or legs 512.

Still further, the muffler 500 includes one or more central baffle segments 518, 520 each defining a central baffle positioned near the center of the expansion chamber (e.g., between the two sets of chevron baffles 514). The central baffles include a longitudinal central baffle defined by baffle segment 518 extending along the muffler axis and terminating at a location spaced-apart from the two most inward chevron baffles 514 as shown, and two offset transverse central baffles defined by baffle segments 520 oriented orthogonal to the longitudinal central baffle segment 518. The transverse central baffle segments 520 may terminate at a location spaced apart from the longitudinal central baffle segment 518 as shown to provide air passages between the baffle segment 518 and the baffle segments 520. As shown in FIG. 14B, the lateral baffle segments 512 may abut only a portion of the interior surface of the chamber, e.g., air passageways 519 may exist between the lateral baffle segments 512 (and the transverse central baffle segments 520) and the inner wall of the expansion chamber.

While the spacing between the various baffles segments 512, 518, and 520 may certainly vary without departing from the scope of the present disclosure, each of the two sets of chevron baffles 514 may be spaced apart from each another (measured between apexes along the muffler axis) by a distance 530 of 12 mm and each may have a baffle segment or leg length 531 of 19 mm, resulting in maximum gap 533 (measured along the mating plane) between each chevron baffle segment and the inner wall of the expansion chamber of 14 mm. Still further, each lateral baffle segment 512 (which again extends parallel with one of the baffle segments of the associated chevron baffle 514) may be offset from its chevron baffle leg by a distance 532 of 3 mm.

FIGS. 15A-15B (singularly and collectively referred to herein as "FIG. 15") illustrate yet another muffler 600 in accordance with embodiments of the present disclosure, wherein FIG. 15A is a top plan view (viewed normal to the mating plane with one symmetric half of the muffler removed), and FIG. 15B is a perspective view thereof. The muffler 600 has: an overall length 640 of 134 mm; a diameter 642 of the inlet port and outlet port of 18 mm; an expansion chamber length 644 of 88 mm; and an expansion chamber diameter 646 of 36 mm. In this embodiment, the muffler 600 includes a series of four, 90-degree chevron baffles 614 (formed by pairs of planar baffle segments 612) generally equally spaced by a distance 630 of 22 mm within the expansion chamber and symmetric about the muffler axis 616 when viewed normal to the mating plane (i.e., each chevron baffle has an apex that again intersects (and is centered along) the muffler axis 616 as shown such that the planar elements or legs 612 of each of the chevron baffles 614 extend at an angle of 45 degrees to the muffler axis). Unlike the chevron baffles of the muffler 500, the chevron baffles 614, as shown in FIG. 15B, generally entirely block (except for the apertures described below) the passage of air moving through the expansion chamber. That is to say, the chevron baffles 614 abut the inner wall of the expansion chamber generally across the entire circumference of the expansion chamber.

As further shown in FIG. 15B, the chevron baffles 614 each define or have formed therethrough one or a series of apertures. More specifically, each chevron baffle has a central aperture 622 having an axis coincident with the muffler axis 616, and a lateral aperture 623 positioned to each side of the central aperture. While not limiting, the apertures may be (when the halves are assembled) generally circular in shape when viewed parallel to the muffler axis 616. Each central aperture 622 may have an effective diameter (when viewed coaxial to the muffler axis 616) of 10 mm, while each lateral aperture 623 may have an effective diameter of 5 mm (when similarly viewed).

Table 2 below provides sound power level measurements for different muffler configurations using the test setup described above and illustrated in FIG. 13. As a baseline, a test was run with the muffler 803 (see FIG. 13) removed (i.e., hose 106 connected directly to the CPAP device 802). After determining the baseline sound power level without a muffler, the mufflers 200, 300, 400, 500, and 600 were evaluated (positioned in place of the muffler 803 in FIG. 13). The results are presented in Table 2.

TABLE 2

| Muffler Present | Blower Pressure, cm H₂O | Muffler Pressure Drop, cm H₂O | Tidal Volume, milliliters | Breaths/ minute | Flow Direction | Sound Power Level, dBA | Delta, dBA |
|---|---|---|---|---|---|---|---|
| None | 10 | N/A | 500 | 20 | N/A | 42.3 | NA |
| 200 | 10 | 0.06 | 500 | 20 | 103 (FIG. 8) | 37.3 | −5 |
| 300 | 10 | 0.28 | 500 | 20 | 301 (FIG. 11) | 36.3 | −6 |
| 400 | 10 | 0.21 | 500 | 20 | 401 (FIG. 12) | 37.6 | −4.7 |
| 500 | 10 | 0.35 | 500 | 20 | 501 (FIG. 14A) | 37.2 | −5.1 |
| 600 | 10 | 0.34 | 500 | 20 | 601 (FIG. 15A) | 35.3 | −7 |

As indicated in Table 2, mufflers in accordance with embodiments of the present disclosure may provide a noticeable reduction in sound power level detected at the user interface/mask (i.e., at the user's head).

Aspects of the invention are enumerated in the claims. However, below is provided a non-exhaustive list of non-limiting examples. Any one or more of the features of these examples may be combined with any one or more features of another example, embodiment, or aspect described herein.

Example Ex1: A positive airway pressure apparatus comprising: a flow generator comprising a housing containing a blower, the blower adapted to produce a flow of pressurized gas at a blower outlet; a user interface; an elongate delivery tube positioned between the flow generator and the user interface, the delivery tube adapted to communicate the flow of pressurized gas from the blower to the user interface; and an inline muffler positioned between the blower and the delivery tube, wherein the muffler comprises a tubular member adapted to attenuate noise associated with the flow of pressurized gas as the gas passes through the muffler, the muffler comprising: an inlet port adapted to operatively couple to the blower outlet; an outlet port adapted to operatively couple to a proximal end of the delivery tube; and a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with the flow of pressurized gas passing through the expansion chamber.

Example Ex2: The apparatus as in example Ex1, wherein the baffles are integrally formed with the body of the muffler.

Example Ex3: The apparatus as in any one of the previous examples, wherein the capture of the sound energy comprises one or more of: destructive interference of sound energy; diffusion of sound energy; attenuation of sound energy; suppression of sound energy; absorption of sound energy; and redirection of sound energy.

Example Ex4: The apparatus as in any one of the previous examples, wherein the inlet port and the outlet port define a muffler axis, and one or more of the baffles comprises two intersecting planar baffle segments defining a chevron.

Example Ex5: The apparatus as in any one of the previous examples, wherein the two intersecting planar baffle segments intersect one another along a line that intersects the muffler axis.

Example Ex6: The apparatus as in any one of the previous examples, wherein the inlet port and the outlet port define a muffler axis, and one or more of the baffles comprises a planar baffle segment integrally formed with the inner wall.

Example Ex7: The apparatus as in any one of the previous examples, wherein the planar baffle segment defines a plane that intersects the muffler axis at an oblique angle.

Example Ex8: The apparatus as in any one of previous examples, wherein the muffler comprises two halves secured to one another.

Example Ex9: The apparatus as in any one of the previous examples, wherein each of the two halves are produced through an injection molding process.

Example Ex10: The apparatus as in any one of the previous examples, wherein the two halves are secured to one another via a process selected from the group comprising ultrasonic welding, bonding, snap-fit engagement, fastening, and overmolding.

Example Ex11: The apparatus as in any one of the previous examples, wherein the baffles comprise an impermeable material.

Example Ex12: The apparatus as in any one of the previous examples, wherein the baffles comprise a plastic material.

Example Ex13: An inline muffler adapted to be positioned within a gas delivery path of a positive airway pressure apparatus between a blower and a user interface, the muffler comprising a tubular housing defined by first and second halves secured to one another, wherein the housing comprises: a first end defining an inlet port; a second end defining an outlet port; and a body extending between the first end and the second end, the body defining an expansion chamber between the first and second ends of the housing, wherein a plurality of baffles extends between opposing inner walls of the expansion chamber, and wherein at least one of the plurality of baffles is formed by a first baffle segment integrally formed with the first half that aligns with a second baffle segment integrally formed with the second half, the two baffle segments comprising distal portions that terminate at or near one another within the expansion chamber.

Example Ex14: The muffler of example Ex13, wherein the plurality of baffles is adapted to interfere with sound energy associated with a flow of pressurized gas passing from the inlet port to the outlet port.

Example Ex15: The muffler as in any one of examples Ex13 to Ex14, wherein one or more of the plurality of baffles comprises a shape selected from one or both of planar baffle segments and curved baffle segments.

Example Ex16: The muffler as in any one of examples Ex13 to Ex15, wherein the first and second baffle segments form a chevron when viewed normal to a mating plane of the first and second halves.

Example Ex17: The muffler as in any one of examples Ex13 to Ex16, wherein one or more of the plurality of baffles defines an aperture.

Example Ex18: The muffler as in any one of examples Ex13 to Ex17, wherein the first and second halves are adapted to be secured to one another via a process selected from the group comprising ultrasonic welding, bonding, snap-fit engagement, fastening, and overmolding.

Example Ex19: The muffler as in any one of examples Ex13 to Ex18, further comprising a compressible seal between the first and second halves.

Example Ex20: The muffler as in any one of claims Ex13 to Ex19, wherein the first and second halves each comprise an impermeable material.

Example Ex21: The muffler as in any one of examples Ex13 to Ex20, where in the first and second halves each comprise a plastic material.

Example Ex22: An inline muffler adapted to be positioned within a gas delivery path of a positive airway pressure apparatus between a blower and a user interface, the muffler comprising: a tubular member adapted to attenuate noise detected at the user interface associated with a flow of pressurized gas produced by the blower, the muffler comprising: an inlet port adapted to operatively couple to an outlet of the blower; an outlet port adapted to operatively couple to a proximal end of a delivery tube that fluidly communicates with the user interface; and a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with the flow of pressurized gas passing through the expansion chamber.

Illustrative embodiments are described and reference has been made to possible variations of the same. These and other variations, combinations, and modifications will be apparent to those skilled in the art, and it should be understood that this disclosure is not limited to the illustrative embodiments set forth herein.

What is claimed is:

1. A positive airway pressure apparatus comprising:
a flow generator comprising a housing containing a blower, the blower adapted to produce a flow of pressurized gas at a blower outlet;
a user interface;
an elongate delivery tube positioned between the flow generator and the user interface, the delivery tube adapted to communicate the flow of pressurized gas from the blower to the user interface; and
an inline muffler positioned between the blower and the delivery tube, wherein the muffler comprises a tubular member adapted to attenuate noise associated with the flow of pressurized gas as the gas passes through the muffler, the muffler comprising:
an inlet port adapted to operatively couple to the blower outlet;
an outlet port adapted to operatively couple to a proximal end of the delivery tube, wherein the inlet port and the outlet port define a muffler axis; and
a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with the flow of pressurized gas passing through the expansion chamber, and wherein one or more of the baffles comprises two intersecting planar baffle segments defining a chevron.

2. The apparatus of claim 1, wherein the baffles are integrally formed with the body of the muffler.

3. The apparatus of claim 1, wherein the capture of the sound energy comprises one or more of: destructive interference of sound energy; diffusion of sound energy; attenuation of sound energy; suppression of sound energy; absorption of sound energy; and redirection of sound energy.

4. The apparatus of claim 1, wherein the two intersecting planar baffle segments intersect one another along a line that intersects the muffler axis.

5. The apparatus of claim 1, wherein the planar baffle segments are integrally formed with the inner wall.

6. The apparatus of claim 1, wherein the muffler comprises two halves secured to one another.

7. The apparatus of claim 6, wherein each of the two halves are produced through an injection molding process.

8. The apparatus of claim 6, wherein the two halves are secured to one another via one of ultrasonic welding, bonding, snap-fit engagement, fastening, and overmolding.

9. The apparatus of claim 1, wherein the baffles comprise an impermeable material.

10. The apparatus of claim 9, wherein the baffles comprise a plastic material.

11. An inline muffler adapted to be positioned within a gas delivery path of a positive airway pressure apparatus between a blower and a user interface, the muffler comprising a tubular housing defined by first and second halves secured to one another, wherein the housing comprises:
a first end defining an inlet port;
a second end defining an outlet port; and
a body extending between the first end and the second end, the body defining an expansion chamber between the first and second ends of the housing, wherein a plurality of baffles extends between opposing inner walls of the expansion chamber, and wherein at least one of the plurality of baffles is formed by a first baffle segment integrally formed with the first half that aligns with a second baffle segment integrally formed with the second half, the two baffle segments comprising distal portions that terminate at or near one another within the expansion chamber.

12. The muffler of claim 11, wherein the plurality of baffles is adapted to capture sound energy associated with a flow of pressurized gas passing from the inlet port to the outlet port.

13. The muffler of claim 11, wherein one or more of the plurality of baffles comprises a shape selected from one or both of planar baffle segments and curved baffle segments.

14. The muffler of claim 11, wherein the first and second baffle segments form a chevron when viewed normal to a mating plane of the first and second halves.

15. The muffler of claim 11, wherein one or more of the plurality of baffles defines an aperture.

16. The muffler of claim 11, wherein the first and second halves are secured to one another via one of comprising ultrasonic welding, bonding, snap-fit engagement, fastening, and overmolding.

17. The muffler of claim 11, further comprising a compressible seal positioned between the first and second halves.

18. The muffler of claim 11, wherein the first and second halves each comprise an impermeable material.

19. The muffler of claim 11, wherein the first and second halves each comprise a plastic material.

20. An inline muffler adapted to be positioned within a gas delivery path of a positive airway pressure apparatus between a blower and a user interface, the muffler comprising:

a tubular housing, the housing comprising:

an inlet port adapted to operatively couple to an outlet of the blower;

an outlet port adapted to operatively couple to a proximal end of a delivery tube that fluidly communicates with the user interface; and a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with a flow of pressurized gas passing through the expansion chamber, and wherein at least one of the baffles comprises first and second baffle segments that define a chevron having an apex centered on a muffler axis defined by the inlet port and the outlet port.

21. A positive airway pressure apparatus comprising:

a flow generator comprising a housing containing a blower, the blower adapted to produce a flow of pressurized gas at a blower outlet;

a user interface;

an elongate delivery tube positioned between the flow generator and the user interface, the delivery tube adapted to communicate the flow of pressurized gas from the blower to the user interface; and an inline muffler positioned between the blower and the delivery tube, wherein the muffler comprises a tubular member adapted to attenuate noise associated with the flow of pressurized gas as the gas passes through the muffler, the muffler comprising:

an inlet port adapted to operatively couple to the blower outlet;

an outlet port adapted to operatively couple to a proximal end of the delivery tube; and a body extending between the inlet port and the outlet port, wherein the body defines an expansion chamber having an effective inner diameter larger than an effective inner diameter of both the inlet port and the outlet port, and wherein an inner wall of the body comprises a plurality of inwardly extending baffles, the baffles adapted to capture sound energy associated with the flow of pressurized gas passing through the expansion chamber, wherein the muffler comprises two halves secured to one another.

* * * * *